US007785874B2

(12) United States Patent
Wickersham et al.

(10) Patent No.: US 7,785,874 B2
(45) Date of Patent: Aug. 31, 2010

(54) COMPOSITIONS AND METHODS FOR MONOSYNAPTIC TRANSPORT

(75) Inventors: Ian R. Wickersham, Brookline, MA (US); John A. T. Young, San Diego, CA (US); Edward M. Callaway, Encinitas, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 12/008,604

(22) Filed: Jan. 11, 2008

(65) Prior Publication Data

US 2008/0193918 A1    Aug. 14, 2008

Related U.S. Application Data

(60) Provisional application No. 60/884,462, filed on Jan. 11, 2007.

(51) Int. Cl.
*C12N 15/63* (2006.01)
*A61K 35/00* (2006.01)
(52) U.S. Cl. .................. 435/320.1; 435/455; 424/93.1; 424/224.1
(58) Field of Classification Search ................ None
See application file for complete search history.

(56) References Cited

U.S. PATENT DOCUMENTS

| 6,033,886 | A | 3/2000 | Conzelmann |
| 6,719,981 | B1 | 4/2004 | Mebatsion et al. |
| 2003/0054340 | A1 | 3/2003 | Friedman et al. |

OTHER PUBLICATIONS

Cronin et al. Curr. Gene Ther. Published on NIH Public Access Feb. 2006 available in PMC, pp. 1-19.*
Watson et al. Mol. Ther. May 2002; 5(5 Pt 1):528-537.*
Parveen et al. Virology 2003, vol. 314, pp. 74-83.*
Sunnayah et al. Physiol. Genomics, Jun. 17, 2004;18(1):25-32. Epub Jun. 17, 2004.*
Aston-Jones & Card, "Use of pseudorabies virus to delineate multisynaptic circuits in brain: opportunities and limitations," *J. Neurosci. Methods*, 103(1):51-61 (2000).
Barnard et al., "Avian sarcoma and leukosis virus-receptor interactions: from classical genetics to novel insights into virus-cell membrane fusion," *Virology*, 344(1):25-9 (2006).
Bates et al., "A receptor for subgroup A Rous sarcoma virus is related to the low density lipoprotein receptor," *Cell*, 74(6):1043-51 (1993).
Braz et al., "Transneuronal tracing of diverse CNS circuits by Cre-mediated induction of wheat germ agglutinin in transgenic mice," *Proc. Natl. Acad. Sci. USA*, 99(23):15148-53 (2002).
Callaway, "A molecular and genetic arsenal for systems neuroscience," *Trends Neurosci.*, 28(4):196-201 (2005).
Cano et al., "Connections of Barrington's nucleus to the sympathetic nervous system in rats," *J. Auton Nerv Syst.*, 79(2-3):117-28 (2000).

DeFalco et al., "Virus-Assisted Mapping of Neural Inputs to a Feeding Center in the Hypothalamus," *Science*, 291(5513):2608-13 (2001).
Enquist, "Exploiting Circuit-Specific Spread of Pseudorabies Virus in the Central Nervous System: Insights to Pathogenesis and Circuit Tracers," *J. of Infect. Dis.*,186:S209-14 (2002).
Etessami et al., "Spread and pathogenic characteristics of a G-deficient rabies virus recombinant: an in vitro and in vivo study," *J. Gen. Virol.*, 81(9):2147-2153 (2000).
Evinger & Erichsen, "Transsynaptic retrograde transport of fragment C of tetanus toxin demonstrated by immunohistochemical localization," *Brain Res.*, 380(2):383-8 (1986).
Finke and Conzelmann, "Virus promoters determine interference by defective RNAs: selective amplification of mini-RNA vectors and rescue from cDNA by a 3' copy-back ambisense rabies virus," *J. Virol.*, 73(5):3818-3825 (1999).
Furuta et al., "In Vivo Transduction of Central Neurons Using Recombinant Sindbis Virus: Golgi-like Labeling of Dendrites and Axons with Membrane-targeted Fluorescent Proteins," *J. Histochem. & Cytochem.*, 49(12):1497-1507 (2001).
Kelly & Strick, "Rabies as a transneuronal tracer of circuits in the central nervous system," *J. Neurosci. Methods*, 103(1):63-71 (2000).
Kuypers & Ugolini, "Viruses as transneuronal tracers," *Trends Neurosci.*, 13(2):71-5 (1990).
Lyon et al., "Disynaptic connections from the superior colliculus to cortical area MT revealed through transynaptic labeling with rabies virus," *Journal of Vision*, 5(8):432 (2005) (Abstract only).
Maskos et al., "Retrograde trans-synaptic transfer of green fluorescent protein allows the genetic mapping of neuronal circuits in transgenic mice," *Proc. Natl. Acad. Sci.*, 99(15):10120-5 (2002).
Mazarakis et al., "Rabies virus glycoprotein pseudotyping of lentiviral vectors enables retrograde axonal transport and access to the nervous system after peripheral delivery," *Hum. Mol. Genet.*, 10(19):2109-121 (2001).
Mebatsion et al., "Budding of rabies virus particles in the absence of the spike glycoprotein," *Cell*, 84(6)941-51 (1996).

(Continued)

*Primary Examiner*—Robert B Mondesi
*Assistant Examiner*—Bao Li
(74) *Attorney, Agent, or Firm*—Klarquist Sparkman, LLP

(57) ABSTRACT

Disclosed herein are methods of expressing a heterologous nucleic acid sequence, such as a sequence encoding a detectable protein, in a primary neuron (or plurality of primary neurons) and other neurons that are monosynaptically connected to the primary neuron (or plurality of primary neurons). Such methods involve viruses (such as, rabies viruses) defective for transsynaptic transport (TST-defective virus) and in situ complementation of the defect in a manner that permits only monosynaptic transport of the TST-defective virus. The TST-defective virus and, therefore, any heterologous nucleic acid sequence it carries in its genome, are not transmitted to neurons that are not monosynaptically connected to the primary neuron (or plurality of primary neurons). Also disclosed are methods of targeting a TST-defective virus to a genetically defined primary neuron (or plurality of primary neurons). The disclosed technology enables far more specific labelling and/or manipulation of neural networks than has previously been possible.

32 Claims, 8 Drawing Sheets
(3 of 8 Drawing Sheet(s) Filed in Color)

OTHER PUBLICATIONS

Melikyan et al., "Low pH is required for avian sarcoma and leukosis virus Env-induced hemifusion and fusion pore formation but not for pore growth," *J. Virol.*, 78(7):3753-62 (2004).

O'Donnell et al., "Interconnected Parallel Circuits between Rat Nucleus Accumbens and Thalamus Revealed by Retrograde Transynaptic Transport of Pseudorabies Virus," *J. Neurosci.*, 17(6):2143-2167 (1997).

Pomeranz et al., "Molecular Biology of Pseudorabies Virus: Impact on Neurovirology and Veterinary Medicine," *Microbio. Mol. Bio. Rev.*, 69(3):462-500 (2005).

Rall et al., "Pathogenesis of Neurotropic Viral Infections," *Fox Chase Cancer Center 2001 Scientific Report*, (2001).

Ruda & Coulter, "Axonal and transneuronal transport of wheat germ agglutinin demonstrated by immunocytochemistry," *Brain Res.*, 249(2):237-46 (1982).

Sandler et al., "Modified herpes simplex virus delivery of enhanced GFP into the central nervous system," *J. Neurosci. Methods.*, 121(2):211-219 (2002).

Schnell et al., "Infectious rabies viruses from cloned cDNA," *EMBO J.*, 13(18):4195-4203 (1994).

Tomioka et al., "Improved Golgi-like visualization in retrogradely projecting neurons after EGFP-adenovirus infection in adult rat and monkey," *J. Histochem. Cytochem.*, 54(5):539-548 (2006).

Ugolini et al., "Retrograde transneuronal transfer of herpes simplex virus type 1 (HSV 1) from motoneurones," *Brain Res.*, 422(2):242-56 (1987).

Ugolini et al., "Transneuronal transfer of herpes virus from peripheral nerves to cortex and brainstem," *Science*, 243(4887):89-91 (1989).

Ugolini, "Specificity of rabies virus as a transneuronal tracer of motor networks: transfer from hypoglossal motoneurons to connected second-order and higher order central nervous system cell groups," *J. Comp. Neurol.*, 356(3):457-80 (1995).

Vercelli et al., "Recent techniques for tracing pathways in the central nervous system of developing and adult mammals," *Brain Res. Bull.*, 51:11-28, (2000).

Wickersham et al., "Monosynaptic Restriction of Transsynaptic Tracing from Single, Genetically Targeted Neurons," *Neuron.*, 53:639-647 (2007).

Wickersham et al., "Retrograde neuronal tracing with a deletion-mutant rabies virus," *Nat. Methods*, 4(1):47-49 (2007).

Wong et al., "Transduction patterns of pseudotyped lentiviral vectors in the nervous system," *Mol. Ther.*, 9(1):101-111 (2004).

Young et al., "Isolation of a Chicken Gene That Confers Susceptibility to Infection by Subgroup A Avian Leukosis and Sarcoma Viruses," *J. Viro.*, 67(4):1811-1816 (1993).

Zou et al., "Genetic tracing reveals a stereotyped sensory map in the olfactory cortex," *Nature*, 414(6860):173-9 (2001).

\* cited by examiner

COMPOSITIONS AND METHODS FOR MONOSYNAPTIC TRANSPORT

CROSS REFERENCE TO RELATED APPLICATIONS

This application claims the benefit of U.S. Provisional Application No. 60/884,462, filed Jan. 11, 2007, which application is incorporated herein in its entirety.

STATEMENT OF GOVERNMENT SUPPORT

This invention was made with United States government support pursuant to grant no. MH63912 from the National Institute of Mental Health (NIMH), grant no. EY10742 from the National Eye Institute (NEI), grant no. DA018828 from the National Institute on Drug Abuse (NIDA), and grant no. CA70810 from the National Cancer Institute (NCI); the United States government has certain rights in the invention.

FIELD OF THE DISCLOSURE

This disclosure concerns methods and compositions (such as kits and their components) useful for identifying, monitoring, or affecting the function of neurons monosynaptically connected to a single primary neuron or plurality of primary neurons of interest.

BACKGROUND

Recent advances in the knowledge of the complexity and specificity of neural circuits suggest that understanding how neural circuits generate perception and behavior will be nearly impossible with presently available techniques. Because different neuron types involved in distinct subcircuits are intermingled, and even neighboring neurons of the same type differ in their connectivity and function (DeAngelis et al., *J. Neurosci.*, 19:4046-64, 1999; Song et al., *PLoS Biol.*, 3:e68, 2005; Ohki et al., *Nature*, 433:597-603, 2005; Yoshimura et al., *Nature*, 433:868-73, 2005), methods are required which can reveal the connections both of specific cell types and especially of single neurons.

Historically, the identification of neural networks has involved labor-intensive and technologically challenging methods, such as examining sections of neural tissue with light or electron microscopy (Gilbert, *Ann. Rev. Neurosci.*, 6:217-47, 1983; Douglas and Martin, *Ann. Rev. Neurosci.*, 27:419-51, 2004; Gray, *Nature*, 183(4675):1592-3, 1959; Timofeeva et al., *J. Neurosci.*, 25(40):9135-43, 2005), simultaneous patch recording from pairs of neural cells (Mercer, et al., *Cereb. Cortex*, 15(10):1485-96, 2005), and photostimulation-based mapping of connections in brain slices (Callaway and Katz, *Proc. Natl. Acad. Sci. USA*, 90(16):7661-5, 1993; Shepherd and Svoboda, *J. Neurosci.*, 25(24):5670-9, 2005; Zarrinpar & Callaway, *J. Neurophysiol.*, 95(3):1751-61, 2006). None of these methods permit a wholesale way of identifying neurons that are connected either to some other cell group or, especially, to a single cell.

Transsynaptic tracers (DeFalco et al., *Science*, 291:2608-13, 2001; Zou et al., *Nature*, 414:173-9, 2001; Braz et al., *Proc. Natl. Acad. Sci. USA*, 99:15148-53, 2002; Maskos et al., *Proc. Natl. Acad. Sci. USA*, 99:10120-5, 2002), out of all the available techniques, might appear to offer a solution to this problem: By introducing a tracer into a particular cell or cell type, synaptically connected cells should be labeled by the tracer and therefore be identifiable as those in synaptic contact with the starting cells in question. Transsynaptic tracers can be introduced into particular neurons or populations of neurons using a variety of methods (Maskos et al., *Proc. Natl. Acad. Sci. USA*, 99(15):10120-5, 2002; DeFalco et al., *Science*, 291(5513):2608-13, 2001; Zou et al., *Nature*, 414(6860):173-9, 2001; Braz et al., *Proc. Natl. Acad. Sci. USA*, 99(23):15148-53, 2002; Ruda & Coulter, *Brain Res.*, 249(2):237-46, 1982; Evinger & Erichsen, *Brain Res.*, 380 (2):383-8, 1986; Ugolini et al., *Brain Res.*, 422(2):242-56, 1987; Ugolini et al., *Science*, 243(4887):89-91, 1989; Kuypers & Ugolini, *Trends Neurosci.*, 13(2):71-5, 1990; Ugolini, *J. Comp. Neurol.*, 356(3):457-80, 1995; Kelly & Strick, *J. Neurosci. Methods*, 103(1):63-71, 2000; Aston-Jones & Card, *J. Neurosci. Methods*, 103(1):51-61, 2000). However, no such method has been sensitive enough to label cells synaptically connected to a single cell of origin.

Moreover, due to their dependence on cellular machinery for transport to and across synapses (Vercelli et al., *Brain Res. Bull.*, 51:11-28, 2000), traditional transsynaptic tracers cross different synapses at different rates: The more hardware servicing in a given connection, the more efficiently it will be traversed by a traditional tracer. As shown schematically in FIG. 1, tracer that accrues in transsynaptically labeled cells will begin spreading in turn to the cells that are connected to them and in fact can label the most strongly connected of these even before weakly connected synaptic partners of the starting population (Ugolini et al., *Brain Res.*, 422:242-56, 1987; Ugolini et al., *J. Comp. Neurol.*, 356:457-80, 1995). The result of asynchronous transsynaptic transfer is an inescapable ambiguity in the number of synapses crossed by traditional transsynaptic tracers.

No technique to date has been capable of identifying en masse neurons that are connected directly to a primary neuron (or population of primary neurons) of interest. The best available tools, transsynaptic tracers, cross multiple synapses and are unable to distinguish weak direct connections from strong indirect ones (Ugolini et al., *Brain Res.*, 422:242-56, 1987; Ugolini et al., *J. Comp. Neurol.*, 356:457-80, 1995). Furthermore, no tracer has proven potent enough to label any connected neurons whatsoever when starting from a single cell. Thus, there is a need for a tracer that crosses one synaptic step, to cells directly connected to the starting cell or cell population, and then stops, unable to spread beyond them to indirectly connected cells.

SUMMARY OF THE DISCLOSURE

Disclosed herein are methods of, and compositions (including kits) for, expressing a heterologous nucleic acid sequence, such as a sequence encoding a detectable protein, in a primary neuron (or plurality of primary neurons) and other neurons that are monosynaptically connected to the primary neuron (or plurality of primary neurons). In particular examples such methods involve viruses (such as rabies viruses) defective for transsynaptic transport (TST) (TST-defective virus) and in situ complementation of the defect in a manner that permits only monosynaptic transport of the TST-defective virus. The TST-defective virus and, therefore, any heterologous nucleic acid sequence it carries in its genome, are not transmitted to neurons that are not monosynaptically connected to the primary neuron (or plurality of primary neurons). Also disclosed are methods of targeting a TST-defective virus to a genetically defined primary neuron (or plurality of primary neurons). The disclosed technology enables far more specific labelling and/or manipulation of neural networks than has previously been possible.

The foregoing and other features will become more apparent from the following detailed description of several embodiments, which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows a wild-type rabies viron. The viral core consists of a helically wound negative-strand RNA genome, which is associated with the nucleocapsid protein (N), matrix protein (M) and with the viral polymerase composed of the phosphoprotein (P) and large protein (L). The viral core is surrounded by a membrane or envelope into which is embedded the viral glycoprotein (G). FIG. 2B diagrams the rabies virus genome and shows the substitution of the EGFP gene in place of the coding sequence for the viral glycoprotein (G) to produce the SADΔG-EGFP viral genome. FIG. 2C illustrates that the glycoprotein-deleted virus (SADΔG-EGFP) can replicate its core to high copy number within initially infected cells and strongly express the transgene, EGFP; however, due to the lack of viral glycoprotein, the newly synthesized viral cores will be unable to spread beyond the initially infected cells.

As illustrated in FIG. 3A, an exemplary TST-defective virus, for instance, a deletion mutant tracing virus missing one or more genes required for transsynaptic spread, and the missing viral gene(s) are introduced into a primary neuron or population of primary neurons of interest. Both the initial infection and the complementing viral gene(s) are restricted to the primary neuron or neuronal population of interest. As illustrated in FIG. 3B, because all viral genes are present in the initially infected neuron or population of neurons, the virus can spread transsynaptically only to cells in direct synaptic contact with them; however the virus cannot spread further since the missing viral genes are not present in the secondary neuron(s).

FIG. 4A shows a mutant tracing virus from which the native glycoprotein (G) gene has been deleted and which has been pseudotyped with a chimeric glycoprotein (designated by "EnvA") consisting of the extracellular and transmembrane domains of the envelope protein from subgroup A avian sarcoma and leukosis virus (ASLV-A) and the intracellular domain of rabies virus glycoprotein. ASLV-A-pseudotyped mutant virus (SADΔG-EGFP(EnvA)) cannot infect mammalian neurons unless such neurons express the gene encoding the ASLV-A receptor, TVA, and thereby expressed the TVA receptor on the neuron surface. A primary neuron (or population of neurons) are provided (for example, by transfection) nucleic acid sequences encoding the TVA receptor, so the virus can enter the primary neuron, and the gene for the rabies virus glycoprotein, so the virus can spread to synaptically coupled secondary neurons. Then, the primary neuron(s) is contacted with the ASLV-A-pseudotyped, G gene-deletion mutant virus. As illustrated in FIG. 4B, the foregoing conditions will result in specific infection of the TVA-expressing primary neuron(s); complementation with the rabies virus glycoprotein allows the virus to spread to monosynaptically connected secondary neurons. Both the primary and secondary neurons will express the EGFP encoded by the viral genome, but the virus can not spread beyond the secondary neurons because those cells do not express the rabies virus glycoprotein.

FIG. 5B shows a single neuron in the field (indicated by a dotted line) that fluoresced in the DsRed2 channel, which indicates this cell was transfected with plasmids encoding DsRed2, TVA, and rabies virus glycoprotein. FIG. 5C shows that the same neuron as in panel B (indicated by a dotted line) fluoresced in the red (DsRed2) and green (EGFP) channels, which indicates that this neuron was selectively infected by SADΔG-EGFP(EnvA). A cluster of neurons surrounding the initially infected cell fluoresced only in the green (EGFP) channel, indicating the presence of the SADΔG-EGFP (EnvA) virus (but not the plasmid DNA, for instance, encoding rabies virus glycoprotein) in such secondary cells. FIG. 5A shows long-range viral spread from the single initially infected cell. In addition to the cluster of green cells immediately surrounding the red/green-fluorescent primary neuron, there were other dense clusters of green (EGFP)-fluorescing cells in the superficial cortical layers immediately above the primary neuron and in distant deep-layer pyramidal cells. The green fluorescence of these more distant neurons is consistent with retrograde transport of the SADΔG-EGFP (EnvA) virus along known projections from the superficial layers to deeper ones and with known patterns of long-range intralaminar connectivity. Scale bars, 200 μm.

FIG. 6A is a DIC image of slice and recording pipettes targeted to putatively pre- and postsynaptic neurons. FIG. 6B shows dual-channel fluorescence (DsRed2 and EGFP labeling) in the same field as in panel A. FIGS. 6C and D show the single channel fluorescence of the same field as in panel A. Specifically, panel C shows EGFP (green) fluorescence and panel D show DsRed2 (red) fluorescence. FIG. 6E shows action potentials in the putatively presynaptic (green-labelled) cell and the coincident inhibitory postsynaptic currents in the putatively postsynaptic (red/green-labelled) cell. FIGs. F-I are analogous to panels A-D, except that action potentials in the putatively presynaptic (green-labelled) cell lead to coincident excitatory postsynaptic currents in the putatively postsynaptic (red/green-labelled) cell. Scale bar, 100 μm (same for each panel).

FIG. 8 shows expression of nGFP (nuclearly-localized EGFP; for instance, EGFP fused to a nuclearly-localized protein (histone)) from RG-pseudotyped, helper lentivirus and mCherry from dG-mCherry rabies. The helper virus expresses both RG and nGFP.

FIG. 9 shows selective infection of cre-expressing cerebellar Purkinje cells with EnvA-dG-GFP rabies, and transsynaptic spread following transcomplementation.

SEQUENCE LISTING

Figure 1:
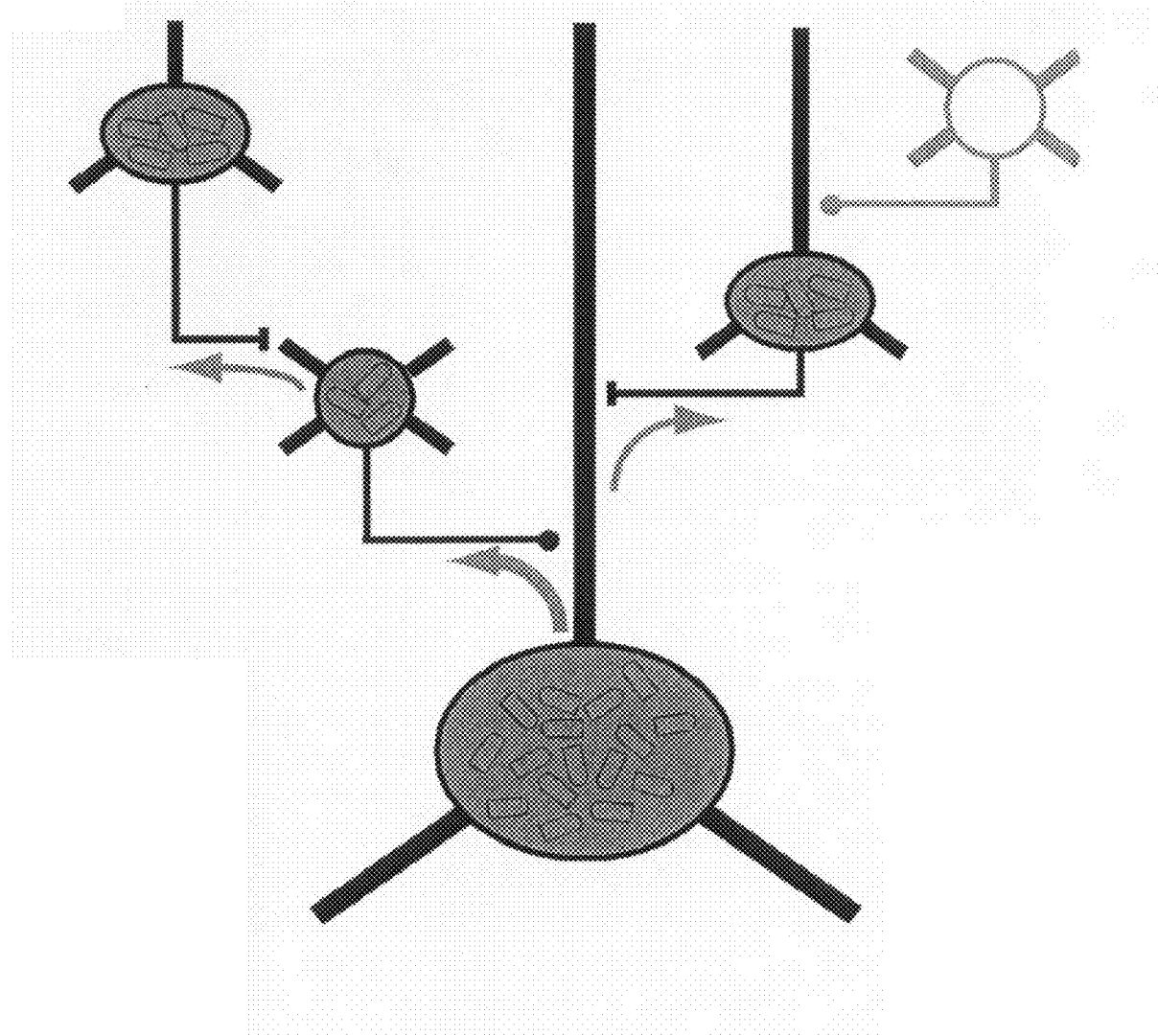
FIG. 1 is a schematic diagram showing that presently known transsynaptic tracers cross multiple synapses at different rates.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is a forward primer for amplification of a nucleic acid sequence encoding the extracellular and transmembrane domains of the ASLV-A envelope protein.

SEQ ID NO: 2 is a reverse primer for amplification of a nucleic acid sequence encoding the extracellular and transmembrane domains of the ASLV-A envelope protein.

SEQ ID NO: 3 is a forward primer for amplification of a nucleic acid sequence encoding the cytoplasmic domain region of the SAD B19 glycoprotein.

SEQ ID NO: 4 is a reverse primer for amplification of a nucleic acid sequence encoding the cytoplasmic domain region of the SAD B19 glycoprotein.

SEQ ID NO: 5 is a primer for introducing a PpuMI site into the rabies virus antigenome downstream of the transcription start signal.

SEQ ID NO: 6 is a primer for introducing a NheI site into the rabies virus antigenome upstream of the transcriptional stop/polyadenylation.

SEQ ID NO: 7 is the nucleotide sequence around the transcriptional start and translation initiation sites of the G gene in pSAD L16.

SEQ ID NO: 8 is the nucleotide sequence around the transcription stop and polyadenylation signal of the G gene in pSAD L16.

SEQ ID NO: 9 is the nucleotide sequence around the PpuMI recognition site in pSADΔG.

SEQ ID NO: 10 is the nucleotide sequence around the transcriptional start and translation initiation sites of the EGFP gene in pSADΔG-EGFP.

SEQ ID NO: 11 is the nucleotide sequence around the transcription stop and polyadenylation signal of the EGFP gene in pSADΔG-EGFP.

DETAILED DESCRIPTION

I. Introduction

Disclosed herein are methods for monosynaptic transport of a heterologous nucleic acid sequence. Such methods can include contacting one or more primary neurons (for instance, a single neuron), each of which is connected by a plurality of synapses to a plurality of secondary neurons, with:
  (i) a virus defective for transport across the plurality of synapses (TST-defective virus), wherein the TST-defective virus includes a heterologous nucleic acid sequence; and
  (ii) one or more nucleic acid molecules encoding one or more polypeptides that complement in trans the TST-defective phenotype of the TST-defective virus, and which nucleic acid molecule(s) and polypeptide(s) are not substantially transported across the plurality of synapses;

under conditions that permit expression of the polypeptide(s) in the primary neuron(s), rescue of the TST-defective phenotype by the polypeptide(s) in the primary neuron, and transport of the TST-defective virus from the primary neuron(s) to the plurality of secondary neurons across the plurality of synapses. In some method embodiments, the one or more trans-complementing polypeptides (for instance, viral polypeptides) are not substantially expressed in neurons in the absence of the one or more nucleic acid molecules encoding such polypeptides. In other exemplary methods, the TST-defective virus is microinjected into the primary neuron(s).

In some method embodiments, the one or more primary neurons are post-synaptic to the plurality of secondary neurons. For instance, the TST-defective virus is transported retrogradely from the primary neuron(s) to the plurality of secondary neurons, and/or is transported anterogradely from the primary neuron(s) to the plurality of secondary neurons. Exemplary TST-defective viruses for using in a disclosed method are RNA viruses, such as negative-strand ssRNA viruses, such as members of the Family Rhabdoviridae (for example, viruses of the genus Lyssavirus, such as rabies virus).

In particular exemplary methods, the TST-defective virus lacks at least one envelope protein (for instance, one or more glycoproteins), and, in some such methods, the trans complementing polypeptide is the at least one envelope protein (for instance, one or more glycoproteins) (or a functional equivalent) lacked by the TST-defective virus. In still other method embodiments, the heterologous nucleic acid sequence encodes a detectable polypeptide, a polypeptide that affects a function of primary neurons or secondary neurons, a polypeptide useful for monitoring a function of primary neurons or secondary neurons, or an inhibitory RNA (RNAi). Exemplary detectable polypeptides include but are not limited to a fluorescent protein, such as green fluorescent protein, red fluorescent protein, yellow fluorescent protein, cyan fluorescent protein, blue fluorescent protein, or a combination thereof.

Some method embodiments involve a TST-defective virus that includes a foreign envelope protein (such as a glycoprotein of a non-neurotropic virus). In some methods, the foreign envelope protein is a chimeric glycoprotein comprising the cytoplasmic domain of the rabies virus glycoprotein and the extracellular and transmembrane domains of a glycoprotein of a non-neurotropic virus (such as avian sarcoma and leucosis virus subgroup A (ASLV-A)). In certain methods involving a TST-defective virus that includes a foreign envelope protein, the one or more primary neurons are further contacted with a nucleic acid molecule encoding a receptor specific for the foreign envelope protein.

Optionally, some methods also involve detecting the TST-defective virus. Some useful means of detection in such optional methods include contacting the primary neuron(s) and the plurality of secondary neurons with a binding agent specific (for instance, monoclonal or polyclonal antibody or nucleic acid probe) for a heterologous polypeptide encoded by the TST-defective virus or specific for a non-host nucleic acid sequence of the TST-defective virus. In specific method embodiments, the detected non-host polypeptide is an envelope protein (such as a glycoprotein). In other exemplary methods, the TST-defective virus is detected substantially only in the primary neuron(s) and the plurality of secondary neurons.

Also disclosed herein are neuron labeling methods, which involve contacting one or more primary neurons, each of which is connected to a plurality of secondary neurons by a plurality of synapses, with:
(i) a virus defective for transport across the plurality of synapses (TST-defective virus), which TST-defective virus includes a foreign envelope protein;
(ii) at least one nucleic acid molecule that:
 (a) encodes one or more polypeptides that complements in trans the TST-defective phenotype of the TST-defective virus; wherein the one or more polypeptides are not substantially transported across the plurality of synapses;
 (b) encodes a receptor specific for the foreign envelope protein; and
 (c) is not substantially transported across the plurality of synapses;

under conditions that permit expression of the polypeptide(s) and the receptor in the primary neuron(s), rescue of the TST-defective phenotype of the primary neuron(s) by the polypeptide, and retrograde transport of the TST-defective virus from the primary neuron(s) to the plurality of secondary neurons across the plurality of synapses; and detecting the TST-defective virus.

In some such methods, the at least one nucleic acid molecule that encodes the polypeptide(s), and the at least one nucleic acid molecule that encodes the receptor are the same nucleic acid molecule. While, in other method embodiments, the at least one nucleic acid molecule that encodes the polypeptide(s), and the at least one nucleic acid molecule that encodes the receptor are different nucleic acid molecules. In some exemplary methods, the one or more primary neurons are first contacted with the at least one nucleic acid molecule and, then, contacted with the TST-defective virus; for example, the one or more primary neurons are contacted with the TST-defective virus at least about two hours after contact with the at least one nucleic acid molecule. Applicable features of disclosed methods for monosynaptic transport of a heterologous nucleic acid sequence also can be a feature(s) of a disclosed neuron labeling methods.

Other disclosed neuron labeling methods involve contacting one or more primary neurons, each of which is connected to a plurality of secondary neurons by a plurality of synapses, with:
(i) a neurotropic virus, which is defective for its native glycoprotein and which includes a foreign glycoprotein from a non-neurotropic virus;
(ii) at least one nucleic acid molecule that:
 (a) encodes a neuron-specific viral glycoprotein, which glycoprotein is not substantially transported across the plurality of synapses;
 (b) encodes a receptor specific for the foreign glycoprotein; and
 (c) is not substantially transported across the plurality of synapses;

under conditions that permit expression of the neuron-specific viral glycoprotein and the receptor in the primary neuron(s), and retrograde transport of the virus from the primary neuron(s) to the plurality of secondary neurons across the plurality of synapses; and detecting the virus.

More particular neuron labeling methods disclosed herein involve contacting one or more primary neurons, each of which is connected to a plurality of secondary neurons by a plurality of synapses, with:
(i) a rabies virus defective for its native glycoprotein, which virus comprises:
 (a) a chimeric glycoprotein comprising the cytoplasmic domain of a rabies virus glycoprotein and an extracellular domain and a transmembrane domain of an avian sarcoma and leucosis virus subgroup A (ASLV-A) glycoprotein, and
 (b) a viral genome, comprising a nucleic acid sequence that encodes a detectable polypeptide;
(ii) at least one nucleic acid molecule that:
 (a) encodes the native viral glycoprotein;
 (b) encodes a receptor specific for the ASLV-A extracellular domain; and
 (c) is not substantially transported across the at least one synapse;

under conditions that permit expression of the native viral glycoprotein, the receptor, and the detectable polypeptide in the primary neuron(s), and retrograde transport of the rabies virus from the primary neuron(s) to the plurality of secondary neurons across the plurality of synapses; and detecting the detectable protein.

Also disclosed herein are methods for monosynaptic transport of a virus defective for transsynaptic transport (TST-defective virus), comprising contacting one or more primary neurons, each of which is connected by a plurality of synapses to a plurality of secondary neurons, with:
(i) a TST-defective virus; and
(ii) one or more nucleic acid molecules encoding one or more polypeptides that complement in trans the TST-defective phenotype of the TST-defective virus, and which nucleic acid molecule(s) and polypeptide(s) are not substantially transported across the plurality of synapses;

under conditions that permit expression of the polypeptide(s) in the primary neuron(s), rescue of the TST-defective phenotype by the polypeptide(s) in the primary neuron, and transport of the TST-defective virus from the primary neuron(s) to the plurality of secondary neurons across the plurality of synapses. Applicable feature(s) of any disclosed method for monosynaptic transport of a heterologous nucleic acid sequence also can be a feature(s) of a disclosed method for monosynaptic transport of a TST-defective virus.

II. Abbreviations and Terms

ASLV-A subgroup A avian sarcoma and leukosis virus
ChR2 channelrhodopsin
NpHR halorhodopsin
DIC differential interference contrast
RG Rabies glycoprotein
RV Rabies virus
TST transsynaptic transport
nGFP nuclearly-localized EGFP Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Foreign envelope protein: An envelope protein that is not encoded by the wild-type genome of the virus in which the envelope protein is found. A foreign envelope can be, but typically is not for purposes of this disclosure, encoded by a heterologous nucleic acid sequence in the genome of the virus in which the envelope protein is found. Preferably, the foreign envelope protein is provided in trans during the assembly of viral particles and during such assembly the foreign envelope protein is incorporated into the viral envelope.

Heterologous nucleic acid sequence: A nucleic acid sequence that is not normally (for instance, in the wild-type sequence) found adjacent to a second nucleic acid sequence. A heterologous nucleic acid sequence, typically, is introduced into its context (for instance, a genomic DNA sequence) by genetic engineering. As described herein, a heterologous nucleic acid sequence encodes a polypeptide and, thus, is capable of being transcribed into an RNA transcript (for instance, an mRNA that is translated into a polypeptide or, for instance, an antisense RNA). Regulatory control sequences other than those that might be useful or needed to transcribe or translate the coding sequence of the heterologous nucleic acid sequence are not contemplated within the meaning of the term in this disclosure. In comparison, a "native" nucleic acid sequence is one that has not been introduced into its context (for instance, genomic DNA sequence) by genetic engineering; thus, for example, a native nucleic acid sequence is normally found in a wild-type genome (for instance, a wild-type viral genome). A native polypeptide is encoded by a native nucleic acid molecule.

Monosynaptic transport: Movement of a composition (such as a viral particle or its progeny) from one neuron to directly synaptically connected neurons with no substantial movement of such composition from the directly synaptically connected neurons to higher-order neurons. No particular mechanism leading to the specified movement is implied or required for purposes of this disclosure. Any mechanism of movement from one neuron to directly synaptically connected neurons that is inherent to the composition in the particular context is intended.

Neuron: A cell within the nervous system that is specialized to send and receive electrical and/or chemical signals. A "primary neuron" is any neuron that includes (or will include) a TST-defective virus and one or more nucleic acid sequences that trans complement the TST defect of the virus. A primary neuron may be found in an intact nervous system structure (such as the brain or spinal cord of a living subject), a nervous system tissue culture (such as a brain slice), or neuronal cell culture (for instance, dispersed neurons in culture). As used herein, the term "primary neuron" is to be distinguished from a primary neuron culture in which neurons in a neuron-containing organ or tissue are dispersed from such organ or tissue and are placed in cell culture. A primary neuron as used herein may be a neuron found in a primary neuron culture; however, the converse is not true, for instance, each neuron in a primary neuron culture is not necessarily a "primary neuron" as used herein. A "secondary neuron" is any neuron (or plurality of neurons) directly synaptically connected to a primary neuron that does not express one or more nucleic acid sequences that trans complement a TST defect of a TST-defective virus. A secondary neuron can be a post-synaptic neuron with reference to a particular primary neuron or can be a pre-synaptic neuron with reference to a particular primary neuron. A "higher-order neuron" is any neuron indirectly (for instance, not directly) synaptically connected to a primary neuron.

Transsynaptic transport (TST)-defective: A failure of a composition (such as a viral particle or its progeny) to be detectably moved (by any applicable mechanism) from one neuron to directly synaptically connected neurons (for instance, across the synapses between such neurons). A composition (such as a viral particle or its progeny) having a TST defect will not, without intervention, be substantially detected in any cell other than the neuron in which the composition (such as a viral particle or its progeny) is found. "Rescue or complementation of a TST-defective phenotype" (or similar language) means that a TST-defective composition (such as a viral particle or its progeny) has recovered an ability to detectably move (by any applicable mechanism) from one neuron to directly synaptically connected neurons (for instance, across the synapses between such neurons); however, for purposes of this disclosure, such rescue or complementation occurs only as long as the neuron (for instance, primary neuron) in which the TST-defective composition (such as a viral particle or its progeny) is located expresses one or more nucleic acid sequences that trans complement the TST defect of the TST-defective composition (for instance, viral particle or its progeny).

Unless otherwise explained, all technical and scientific terms used herein have the same meaning as commonly understood by one of ordinary skill in the art to which this disclosure belongs. The singular terms "a," "an," and "the"

include plural referents unless context clearly indicates otherwise. Similarly, the word "or" is intended to include "and" unless the context clearly indicates otherwise. "Comprising" means "including." Hence "comprising A or B" means including A, or B, or A and B. All publications, patent applications, patents, and other references mentioned herein are incorporated by reference in their entirety to the extent permitted by applicable laws and rules.

Materials, methods, and examples are illustrative only and not intended to be limiting. Methods and materials similar or equivalent to those described herein can be used in the practice or testing of the disclosed technology (see, for instance, Sambrook et al., *Molecular Cloning: A Laboratory Manual*, 2d ed., Cold Spring Harbor Laboratory Press, 1989; Sambrook et al., *Molecular Cloning. A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology. A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999).

III. Methods

A long-standing challenge in the field of neuroscience has been how to structurally and functionally dissect complex neural networks. In particular, there previously has been no feasible way to structurally identify or functionally monitor or manipulate one or more "monosynaptic network(s)," each such network consisting of a single neuron of origin (particular examples of which are referred to herein as a "primary neuron"; for other examples see Section II and elsewhere in this disclosure) and some (for instance, a substantial number) or all of the neurons to which the originating neuron is monosynaptically connected. Neurons monosynaptically connected to a primary neuron may be referred to herein as "secondary neurons" (see, also, Section II and elsewhere in this disclosure for further description of secondary neurons).

Monosynaptic connections to a primary neuron include synapses between the primary neuron and presynaptic secondary neurons and synapses between the primary neuron and postsynaptic secondary neurons; the former synapses providing input to the primary neuron and the latter synapses transmitting output from the primary neuron.

A variety of neurotropic viruses are known to be transported between neurons (for instance, across synapses) unidirectionally or bidirectionally. Unidirectional transsynaptic transport of such viruses can be anterograde, for instance, from presynaptic to postsynaptic neuron, or retrograde, for instance, from postsynaptic to presynaptic neuron. Several such viruses have been used as traditional transsynaptic tracers (for instance, pseudorabies virus and alpha-herpesviruses (such as pseudorabies virus and herpes simplex virus type 1)). Infective, replication-competent neurotropic viruses will continue to cross synapse after synapse while replication-defective neurotropic viruses will not cross even a single synapse.

This disclosure fills the gap by describing compositions and corresponding methods useful to identify, monitor, and/or manipulate a primary neuron (or a plurality of primary neurons) and some or substantially all of its presynaptic or postsynaptic secondary neurons, or to identify, monitor, and/or manipulate a primary neuron (or a plurality of primary neurons) and some or substantially all of its presynaptic or postsynaptic secondary neurons. In general embodiments, the disclosed methods involve mutant viruses that are defective at least for transsynaptic transport (TST-defective virus), introduction of the TST-defective virus (for instance, by infection or otherwise) into a primary neuron or a plurality of primary neurons, and in situ complementation of the viral defect(s) (including the TST defect) in the primary neuron(s). Following trans complementation of its defect(s) (including the TST defect), the virus is competent to spread to some or substantially all of the secondary neurons monosynaptically connected to the primary neuron.

In some embodiments (for instance, non-human transgenic animal models, discussed elsewhere), a particular neuron monosynaptically connected to a primary neuron also expresses nucleic acid sequences necessary to trans complement a TST defect of a TST-defective virus; in which case, that particular neuron would be considered a primary neuron vis a vis secondary neurons monosynaptically connected to it. Secondary neurons do not contain the components necessary for in situ complementation of the viral defect(s) (including the TST defect); therefore, the virus cannot spread beyond the secondary neurons. Optionally, the TST-defective virus is targeted to particular primary neurons.

The disclosed methods contemplate the use of any virus defective for transsynaptic transport (TST-defective virus); provided that the TST defect can be complemented in trans. In the absence of, or upon trans complementation of, the TST defect, an exemplary TST-defective virus can be bidirectionally or unidirectionally transported across a synapse. By selecting for use in some method embodiments a virus that is normally (for instance, in the absence of a TST defect) bidirectionally transported across synapses (for instance, alpha-herpesviruses in their wild form), some or substantially all of a monosynaptic network can be identified, monitored, and/or manipulated. By selecting for use in other method embodiments a virus that is normally transported primarily or exclusively in a retrograde direction (for instance, rabies virus, pseudorabies virus Bartha strain, and/or herpes simplex virus type 1 McIntyre B strain), a primary neuron (or a plurality of primary neurons) and some or substantially all of its presynaptic secondary neurons can be identified, monitored, and/or manipulated. By selecting for use in still other method embodiments a virus that is normally transported primarily or exclusively in an anterograde direction (for instance, HSV-1 strain H129 (Zemanick et al., *Proc. Natl. Acad. Sci. USA*, 88(18):8048-51, 1991; Rinaman and Schwartz, *J. Neurosci.*, 24(11):2782-6, 2004), a primary neuron (or a plurality of primary neurons) and some or substantially all of its postsynaptic secondary neurons can be identified, monitored, and/or manipulated.

In some instances, a TST-defective virus is a neurotropic virus (such as Japanese encephalitis virus, Venezuelan equine virus, California encephalitis virus, polio virus, coxsackie virus, echo virus, mumps virus, measles virus, influenza virus, rabies virus, member of the family Herpesviridae (such as alphaherpesvirinae or betaherpesvirinae, including without limitation herpes simplex virus type 1, pseudorabies virus, varicella-zoster virus, cytomegalovirus, or Epstein-Barr virus), rubella virus, JC polyomavirus, human T-lymphotropic virus 1, human immunodeficiency virus, or combinations thereof). In particular instances, a TST-defective virus is an RNA virus (for example, a negative-strand ssRNA virus or a non-segmented, negative-strand ssRNA virus). Exemplary negative-strand RNA viruses that can be used in the disclosed methods include, but are not limited to: Orthomyxoviruses (such as the influenza virus), Rhabdoviruses (such as Rabies virus), and Paramyxoviruses (examples of which include measles virus, respiratory syncytial virus, and parainfluenza viruses). In more particular instances, an RNA virus is a member of the Family Rhabdoviridae (such as Cytorhabdovirus sp.; Ephemerovirus sp.; Lyssavirus sp.; Novirhabdovirus sp.; Nucleorhabdovirus sp.; Vesiculovirus sp.). Some method embodiments envision the use of a TST-defective Lyssavirus sp. (such as a rabies virus, including any species, strain (for instance, CTN strain, Ni-CE strain, Nishi-gahara strain, CVS strain, strain TS-80 (ARRIW&M, Pokrov, Russia), CVS-11 strain, Pasteur strain, AFX strain) or sub-strain thereof).

In some method embodiments, a TST-defective virus is non-lytic, non-infective, infective, replication defective, or replication competent, or a combination thereof (to the extent that such combination is not functionally impossible, for instance, replication defective and replication competent). In particular examples, a TST-defective virus is non-lytic, or non-infective and replication competent, or replication defective and infective, or replication defective and non-infective, or replication defective.

A trans-complementable TST defect present in a virus useful in disclosed method embodiments can result from any viral mutation that substantially abolishes or significantly attenuates the production in neurons of viral progeny capable of transsynaptic spread. For example, such mutations can be in genes needed for replicating the viral genome, packaging the virus, budding of the virus from a cell membrane or subsequent penetration of the next cell, or virtually any step in replication and cell-to-cell spread of the virus. In some methods, one or more viral genes are deleted, including for example viral genes encoding (a) polymerases or kinases, the deletion of which individually or as a group abolishes or significantly attenuates the replication of the viral genome, (b) envelope glycoproteins, the deletion of which individually or as a group abolishes or significantly attenuates the ability of viral progeny to spread transsynaptically, (c) viral structural proteins, such as capsid or matrix proteins, the deletion of which individually or as a group abolishes or significantly attenuates the synthesis of viral progeny. In other examples, any of the foregoing viral genes have a mutation, such as one or more point mutations, one or more insertion mutations, or one or more deletions of less than the entire gene that substantially abolishes or significantly attenuates the production in neurons of viral progeny capable of transsynaptic spread. Mutations having the desired effect are known in the art (see, for instance, DeFalco et al., *Science,* 291:2608-2613, 2001; Cai et al., *J. Virol.,* 61(3):714-721, 1987). Alternatively, methods of making and/or isolating mutant viruses having the desired characteristics are described herein (see, for instance, Example 1), and other such methods are known in the art.

Trans complementation of the TST-defect in a disclosed method is accomplished by providing to the one or more primary neurons contacted (for instance, infected) or to be contacted by the TST-defective virus one or more nucleic acid molecules encoding one or more polypeptides that complement in trans the TST-defective phenotype of the TST-defective virus. One of ordinary skill in the art will appreciate that the particular nucleic acid molecule(s) and encoded polypeptide(s) used to rescue a TST-defective phenotype in a primary neuron will depend upon the nature of the particular TST-defect. For example, in circumstances where a TST-defect arises due to a deletion or other mutation of one or more viral genes needed for transsynaptic transport, trans complementation can be accomplished by providing a nucleic acid molecule that includes nucleic acid sequences encoding the wild-type or otherwise functional polypeptide product(s) of the deleted or mutated viral gene(s), or other polypeptide(s) of sufficiently similar function as the wild-type polypeptide(s) to rescue the TST defect in the neuron of interest. In situations where a TST defect is trans complemented by the expression of a single polypeptide, only a single trans-complementing nucleic acid molecule encoding such polypeptide need be provided. In other circumstances, the expression of two or more polypeptides are used to rescue a TST defect, in which case, a single nucleic acid molecule encoding all of such trans-complementing polypeptides are used, or, alternatively, multiple nucleic acid molecules encoding one or more of such trans-complementing polypeptides are used.

A trans-complementing nucleic acid molecule useful in the disclosed methods is any nucleic acid molecule that may be introduced into the neuron(s) of interest, can express in the neuron(s) of interest one or more polypeptide(s) that rescue the TST-defective phenotype of a TST-defective virus in that neuron, and is not included in the genome of the TST-defective virus (in which case, the nucleic acid molecule would not be introduced in trans) or included in the genome of a viral vector that is transmitted in whatever manner to neurons synaptically connected to a primary neuron (for instance, by transsynaptic transport or other means of neuronal infectivity). In some method embodiments, a trans-complementing nucleic acid molecule is included in an expression vector, including, without limitation, a plasmid expression vector, or a viral expression vector (that is not transmitted to neurons synaptically connected to a primary neuron). In other method embodiments, a trans-complementing nucleic acid molecule is included in a helper virus (that is incapable of TST or has a TST-defective that is not trans complemented in a primary neuron). Specific, non-limiting examples of such helper viruses include an adenovirus, an HSV amplicon vector, or a lentivirus. Helper viruses can express the trans-complementing nucleic acid molecule as well as other proteins, such as a marker protein (e.g., GFP and others known in the art including those described herein). In some embodiments, the helper virus is a cre-dependent virus (such as a cre-dependent lentivirus or a cre-dependent adenovirus) or an HSV amplicon vector. One skilled in the art will appreciate that other recombinases can be used in place of cre, for example a recombinase that results in excision and reinsertion of at least some of the nucleic acid fragments (such as at least 10%, at least 20% or at least 50%) in a random orientation (referred to as the FRO orientation). For example, recombinases such as Flp, Tn3, and PhiC31 can be used, as well as a recombinase of a DNA transposon, for example a recombinase of Tcl/mariner, hAT, CACTA, P, Mutator, piggyBac, PIF/Harbinger, Transib, or Merlin.

To substantially or fully limit a TST-defective virus to monosynaptic transmission, the combination of TST-defective virus and trans-complementing nucleic acid molecule(s) (and encoded polypeptide(s)) is substantially restricted to the primary neuron(s), for instance, does not substantially occur in any secondary or higher-order neuron. For example, the TST-defective virus, the trans-complementing nucleic acid molecule(s) or both are targeted to particular primary neurons. In particular embodiments, the TST-defective virus is targeted to particular primary neurons, as described in detail elsewhere in this disclosure. In such embodiments, the trans-complementing nucleic acid molecule(s) are either targeted to the same neurons as the TST-defective virus or are delivered in a non-targeted manner or a partially (or somewhat) targeted manner (for instance, targeted to neurons in a similar anatomical location as neurons contacted with (or to be contacted with) the TST-defective virus). In other method embodiments, the trans-complementing nucleic acid molecule(s) are targeted to particular neurons with non-targeted infection by the TST-defective virus; however, in these embodiments, the ordinarily skilled artisan will recognize that the TST-defective virus will be detectable in all neurons in which it resides, and monosynaptic spread of the virus will occur only from those neurons in which both the TST-defective virus and the trans-complementing nucleic acid molecule(s) are found. In methods involving targeting of the trans-complementing nucleic acid molecule and no or limited targeting of the TST-defective virus, primary neurons containing both the TST-defective virus and the trans-complementing nucleic acid molecule(s) are identified by any known method; for example, by designating the neuron(s) into which a trans-complementing nucleic acid molecule(s) was introduced, and/or by detection (for instance, by immunodetection and/or in situ hybridization) of a product (for instance, mRNA or polypeptide) encoded by the trans-complementing nucleic acid molecule(s).

Neurons can be contacted with a TST-defective virus by any known technique(s) that results in at least some virus entering at least some of the contacted neurons. For example, in some embodiments, an infective TST-defective virus (such as a TST-defective virus pseudotyped with its native envelope protein(s) or envelope protein(s) of a different virus) is placed in spatial proximity with a population of neurons in any manner or under conditions that will permit infection of one or more primary neurons by the TST-defective virus. In particular examples, infective TST-defective virus particles are added to the culture medium in which isolated neurons or neuronal tissues (such as brain slices) are being cultured, or infective virus is injected (such as stereotaxically injected or microinjected) into one or more single primary neurons or into a desired neuron-containing organ or tissue (such as the brain or particular regions thereof, and/or into muscle (for instance, skeletal muscle) innervated by neurons of interest). In some embodiments, non-infective TST-defective virus is introduced into primary neurons, for example, by microinjection.

Similarly, in other embodiments, neurons are contacted with trans-complementing nucleic acid molecule(s) by any known technique(s) that results in at least some such nucleic acid molecules virus entering or being present in at least some of the contacted neurons. In some instances, transgenic animals containing in their genome trans-complementing nucleic acid sequences are produced using well-known methods. In particular instances, the expression in a transgenic animal of trans-complementing nucleic acid sequences is substantially limited to a particular tissue type (for instance, neurons) by using a neuron-specific promoter operably linked to the trans-complementing nucleic acid sequence(s) in the transgene used to genetically modify the animal. In other instances, a helper virus with a cell-type specific (for instance, neuron-specific) promoter driving expression of trans-complementing nucleic acid sequences is used (Davis et al., *Endocrinology*, 142:795-801, 2001; Gou et al., *NucleicAcids Res.*, 32:e134, 2004; van den Pol et al., *Neuron*, 42:635-52, 2004). Specific, non-limiting examples of helper viruses include an adenovirus, an HSV amplicon vector, or a lentivirus. In some embodiments, the helper virus is a cre-dependent virus (such as a cre-dependent lentivirus or a cre-dependent adenovirus) or an HSV amplicon vector. In still other method embodiments, trans-complementing nucleic acid molecules are introduced into neurons by known transfection methods, including, without limitation, electroporation (such as single-cell electroporation (Haas et al., *Neuron*, 29:583-91, 2001; Rathenberg et al., *J. Neurosci. Methods*, 126:91-8, 2003)), photoporation, chemical transfection (such as lipofection or calcium phosphate transfection), or physical bombardment (such as with a "gene gun"), or uptake of naked DNA. Trans-complementing nucleic acid molecules also are introduced into primary neurons by microinjection in some method embodiments.

Particular method embodiments useful for identifying, affecting or monitoring a single primary neuron and its monosynaptic pathway in a neuronal tissue culture (such as a brain slice) involve transfecting, by single-cell electroporation or single-cell photoporation, or microinjecting a single primary neuron with one or more (for instance, one) nucleic acid molecule(s) encoding one or more trans-complementing polypeptides for overcoming a virus' TST defect and encoding a receptor specific for an envelope protein of a virus with substantially different tropism from that of a TST-defective virus (for instance, a non-neurotropic virus or a virus having substantially no tropism for the type of cell into which the TST-defective virus is or will be introduced). In some such embodiments, an infective TST-defective virus lacking its native envelope protein gene(s) pseudotyped with the envelope protein of a non-neurotropic virus is added to the culture medium bathing the neuronal tissue culture. In other such embodiments, an infective TST-defective virus lacking its native envelope protein gene(s) pseudotyped with the envelope protein of a virus having substantially no tropism for the neuronal tissue culture cells is added to the culture medium bathing the neuronal tissue culture. In the foregoing embodiments, the TST-defective virus is specifically targeted to the primary neuron(s) transfected with the nucleic acid molecule encoding the foreign envelope protein receptor. Other method embodiments useful for identifying, affecting or monitoring a single primary neuron and its monosynaptic pathway in a neuronal tissue culture (such as a brain slice) involve microinjecting a single primary neuron with one or more (for instance, one or two) trans-complementing nucleic acid molecules and with the TST-defective virus.

Exemplary methods involve a rabies virus with a deletion from its genome of the G gene encoding its envelope glycoprotein (see, for instance, FIG. 2B), or a pseudorabies virus with a deletion from its genome of the gene encoding its thymidine kinase. Thus, for example, a nucleic acid molecule all or part of which encodes the rabies virus glycoprotein (or the glycoprotein of another rhabdovirus species) is used to trans complement the rabies virus G gene-deletion mutant, or a nucleic acid molecule all or part of which encodes the pseudorabies virus thymidine kinase (or the thymidine kinase of another herpesvirus, such as herpes simplex virus type 1) is used to trans complement a pseudorabies virus thymine kinase deletion mutant. Other exemplary methods involve a rabies virus with a deletion from its genome of the N, P, and/or L gene(s); in such embodiments, for example, a nucleic acid molecule all or part of which encodes the deleted N, P, and/or L gene(s) (or functionally equivalent genes of another rhabdovirus species) is used to trans complement the rabies virus gene deletion(s).

In some method embodiments, the genome of the TST-defective virus includes one or more heterologous nucleic acid sequences (such as one, two or three heterologous nucleic acid sequences). In particular embodiments, a heterologous nucleic acid sequence encodes a detectable polypeptide, a polypeptide that affects a function of primary and/or secondary neurons, a polypeptide useful for monitoring a function of primary and/or secondary neurons, a polypeptide to allow temporal control of viral spread (e.g., Cre-ER2, inducible cre recombinase), or an inhibitory RNA (RNAi).

A detectable polypeptide can include, without limitation, a non-host polypeptide for which specific antibodies are available or can be made using techniques common in the art, a fluorescent polypeptide (e.g., marker protein), or an enzyme (such as β-galactosidase, alkaline phosphatase) that catalyzes formation of a detectable reaction product. Exemplary fluorescent proteins including green fluorescent protein (GFP), enhanced GFP (EGFP), Dendra-2. TagGFP, Emerald GFP (EmGFP; Invitrogen), mCherry, LacZ, AcGFP1 fluorescent protein (Evrogen), DsRed fluorescent protein, DsRed-monomer fluorescent protein (Evrogen), TurboRFP (red fluorescent protein derived from the sea anemone *Entacmaea quadricolor*; Evrogen), JRed (red fluorescent protein obtained by mutagenesis of Anthomedusae jellyfish chromoprotein; Evrogen), yellow fluorescent protein (for instance, PhiYFP, TurboYFP; Evrogen), cyan fluorescent protein (CFP; Invitrogen), and blue fluorescent protein (BFP; Invitrogen)].

Polypeptides useful for monitoring and/or affecting a function of a primary neuron and/or its plurality of secondary neurons include, without limitation, sensors of neural activity (Reiff et al., *J. Neurosci.*, 25:4766-78, 2005; Chanda et al., *Nat. Neurosci.*, 8:1619-26, 2005), ion channels (such as photosensitive ion channels (Li et al., *Proc. Natl. Acad. Sci. USA*, 102:17816-21, 2005; Boyden et al., *Nat. Neurosci.*, 8:1263-8, 2005), and/or ligand-sensitive ion channels, for example a $Ca^{++}$ sensor), G-protein coupled receptors (such as allatostatin receptors), synaptophluorin, toxins (such as diphtheria toxin A) or herpes simplex virus (HSV) thymidine kinase (for instance, for use in combination with delivery of gancyclovir), channelrhodopsin (ChR2, a light-gated ion channel that can be used to depolarize neurons with light), or halorhodopsin (NpHR, a light-gated chloride pump that can be used to hyperpolarize neurons with light).

In one example, a sensor of neural activity delivered to one or more monosynaptic networks by a disclosed method, when combined with two-photon imaging in vivo, is expected to permit identification of the functional properties of cells directly connected to an originally identified, functionally characterized, and electroporated postsynaptic neuron (or plurality of such neurons). In another example, expression of a gene encoding a photosensitive ion channel in one or more monosynaptic networks as disclosed herein is expected to permit patterned stimulation of presynaptic cells while recording from the cell(s) on which they converge.

In some embodiments, a heterologous nucleic acid sequence encodes a transactivator (for instance, tTA, rtTA, or Gal4) or recombinase (for instance, Cre, Tn3, or FlpE), which is used, inter alia, to further direct gene expression in synaptically coupled neurons.

A. Exemplary TST-Defective Rabies Virus

The rabies virus is a non-segmented negative-strand RNA virus specialized to infect mammalian nervous systems; Finke and Conzelmann (*Virus Res.*, 111(2):120-131, 2005). The rabies virion is depicted schematically in FIG. 2A. The viral core, consisting of the RNA genome and associated proteins, is surrounded by the host-cell derived phospholipid bilayer envelope or membrane, into which is embedded the trimeric envelope glycoprotein (G). The glycoprotein is responsible for facilitating budding of the rabies virus through the host cell membrane, picking up its envelope and glycoprotein as it does so, for binding to receptors on the presynaptic membrane of the next cell to be infected, and, following endocytosis of the bound virus, for release of the viral core into the cytosol to begin a new cycle of infection (Mebatsion et al., *Cell*, 84(6):941-51, 1996).

Figure 3:
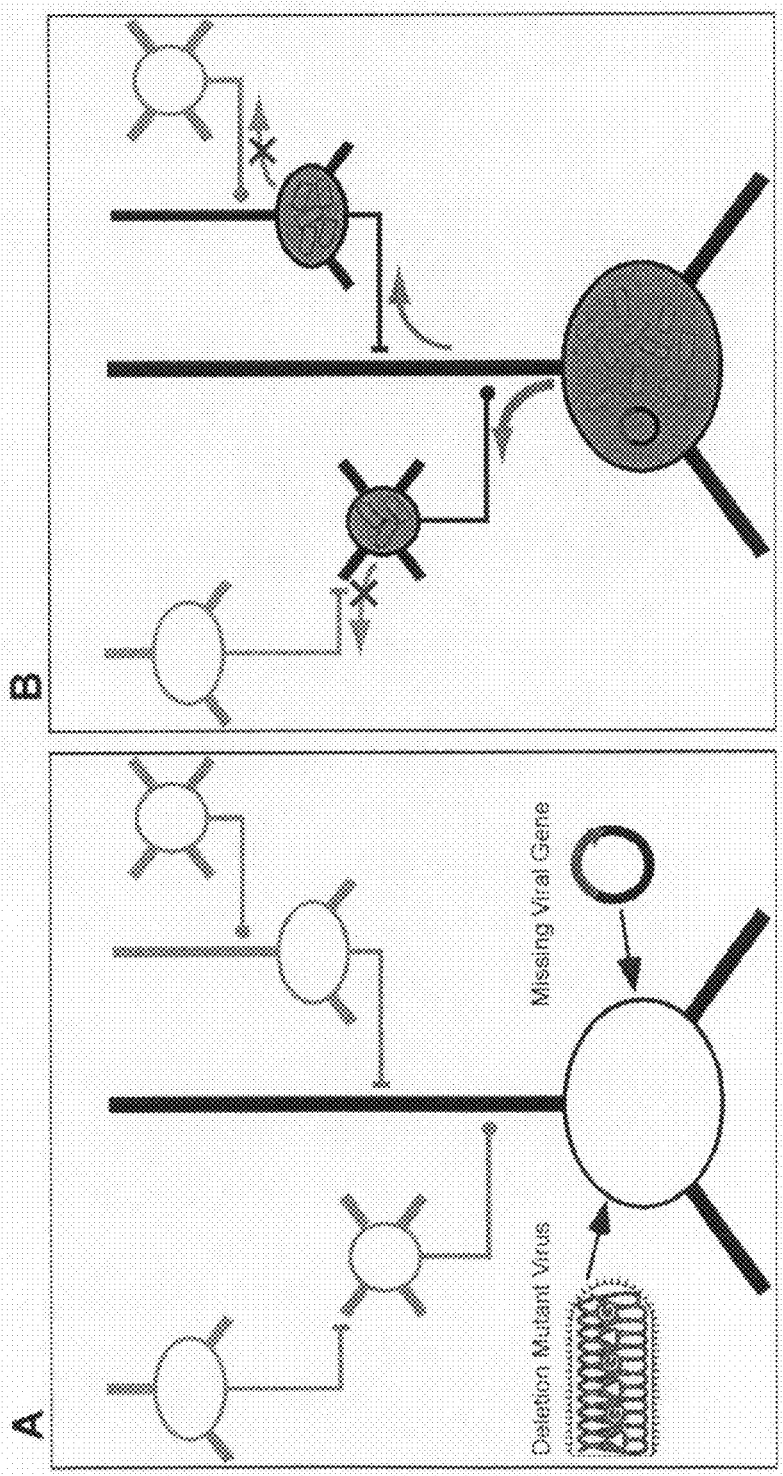
FIG. 3 is a schematic diagram showing one example of monosynaptic restriction of transsynaptic tracing by in situ complementation.

One particular method embodiment described herein involves a rabies virus, which is lacking the glycoprotein (G or RG) gene, required for transsynaptic spread (Mebatsion et al., *Cell*, 84:941-51, 1996; Etessami et al., *J. Gen. Virol.*, 81:2147-53, 2000), and complementation of this vector in situ by providing the missing G gene in trans in the initially infected neuron population only (FIG. 3A). The trans-complemented rabies virus is thus competent to spread to all monosynaptically connected cells (FIG. 3B). Because the trans-complementing genes are not in those secondarily infected cells, however, the rabies virus cannot spread any further.

Figure 2:
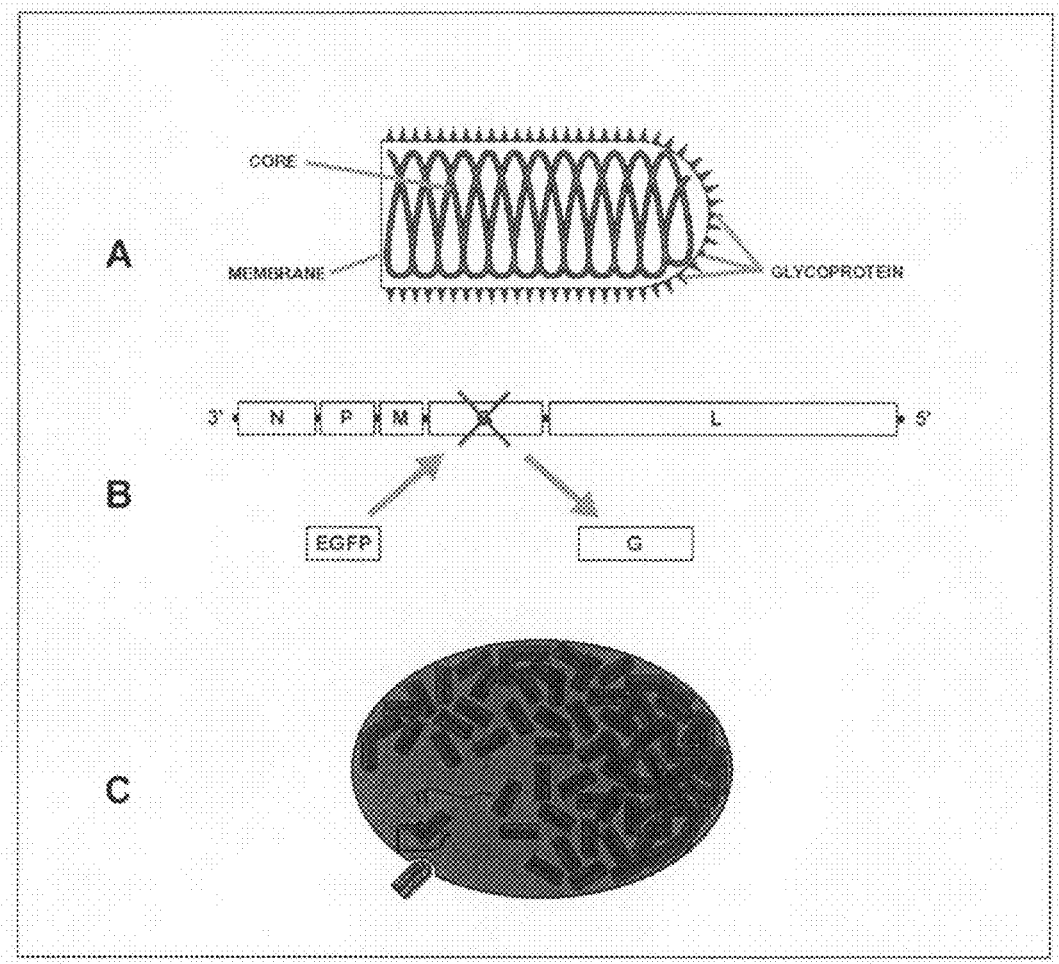
FIG. 2 is a series of schematics diagramming the construction and activity of the recombinant rabies virus SADΔG-EGFP.

Rabies virus is a useful exemplary virus because it has been used with great success in its intact form as a transsynaptic tracer, crossing synapses predominantly or exclusively in the retrograde direction (Ugolini et al., *J. Comp. Neurol.*, 356: 457-80, 1995; Ugolini et al., *Science*, 243:89-91, 1989; Kelly & Strick, *J. Neurosci. Methods*, 103:63-71, 2000; Hoshi et al., *Nat. Neurosci.*, 8:1491-3, 2005; Nassi et al., *Neuron*, 50:319-27, 2006). Although the rabies virus glycoprotein is required for transsynaptic spread, it is not required for transcription of the viral genes or for replication of the genome within infected cells (Mebatsion et al., *Cell*, 84:941-51, 1996). As described in Example 1, a recombinant rabies virus with its glycoprotein gene replaced with that of enhanced green fluorescent protein (EGFP) (FIG. 2B) produces levels of EGFP sufficient to brightly label even the fine dendritic and axonal details of infected neurons and yet it cannot spread beyond these initially infected cells (FIG. 2C).

Advantageously, the rabies virus is less cytotoxic than other tracing viruses (such as pseudorabies virus and herpes simplex virus type 1). No widespread cell death is observed in rabies-virus-infected subjects even following death of the subject (Ugolini, *J. Comp. Neurol.*, 356(3):457-80, 1995), and infected subjects survive substantially longer than those infected centrally by herpesviruses. Rabies virus also is quite infective. For example, tens of thousands of herpesvirus particles may be required to begin an infection following intracerebral injection (Ugolini et al., *Brain Res.*, 422(2):242-56, 1987; Card et al., *J. Comp. Neurol*, 407(3):438-52, 1999; Norgren & Lehman, *Neurosci. Biobehav. Rev.*, 22(6):695-708, 1998); however, only a single infectious unit of rabies virus injected into the brain is sufficient to lead to a full case of rabies (Lafay et al., *Virology*, 183(1):320-30, 1991; Ito et al., *J. Virol.*, 75(19):9121-8, 2001).

B. Optional Detection of a TST-Defective Virus

Some exemplary methods include an optional step in which the TST-defective virus is detected. Such detection is useful, for example, for tracing monosynaptic networks, including a monosynaptic network originating from a single primary neuron. In some methods, detection involves contacting one or more primary neuron(s) and/or its (their) plurality of secondary neurons with a binding agent specific for a non-host polypeptide encoded by the TST-defective virus or specific for a non-host nucleic acid sequence of the TST-defective virus.

A non-host polypeptide encoded by the TST-defective virus includes, for example, any polypeptide encoded by the viral genome, or a polypeptide encoded by a heterologous nucleic acid sequence included the viral genome. Preferably, a non-host polypeptide is not normally expressed in neurons of the host organism (for instance, the organism in which the primary and secondary neurons are located) to avoid cross-reactivity of a specific binding agent with a polypeptide native to the host organism. In method embodiments involving a TST-defective rabies virus, the rabies virus L, G, N, M, or P proteins or a combination thereof are detected. Similarly, a non-host nucleic acid sequence of the TST-defective virus includes, for example, any nucleic acid sequence in the genome of the TST-defective virus that can be detected without significant cross-reactivity with host nucleic acid sequences.

A specific binding agent is one that binds substantially only to a defined target. The nature of the specific binding agent will depend upon the nature of the target. Agents that specifically bind polypeptide targets are well known in the art and include, for example, antibodies and soluble receptors. Antibodies or antibody fragments (for instance, Fab, Fab', (Fab')$_2$, F(ab')$_2$, Fvs, and single-chain Fv) useful for detecting non-host polypeptides in disclosed methods can be purchase from commercial sources or produced using standard procedures (see, for instance, Harlow & Lane, *Antibodies. A Laboratory Manual*, New York: Cold Spring Harbor Laboratory Press, 1988). Agents (such as nucleic acid probes) that specifically bind to nucleic acid sequences are equally well known in the art. Nucleic acid probes specific for a TST-defective virus genome can be purchased commercially and/or be designed and produced using widely available techniques.

Detection of the TST-defective virus may direct or indirect. In some methods, a TST-defective virus encodes a detectable polypeptide that is fluorescent or otherwise directly detected in primary and secondary neurons. Exemplary fluorescent polypeptides are described elsewhere in this disclosure and other examples are well known in the art. In other methods, a TST-defective virus encodes an enzyme (such as β-galactosidase or alkaline phosphatase) that produces under the appropriate reaction conditions a detectable product. Indirect methods of detecting a TST-defective virus also are envisioned. Such indirect detection methods would be known to those of ordinary skill in the art based on the teachings of this disclosure; for example, a non-host polypeptide expressed by a TST-defective virus may be detected by a primary antibody specific for such non-host polypeptide and an enzyme-labeled or otherwise detectable secondary antibody specific for the primary antibody may be used for indirect detection of the TST-defective virus.

C. Optional Targeted Delivery of TST-Defective Virus to Primary Neurons

Some method embodiments contemplate optional targeting of an initial infection by a TST-defective virus to particular primary neurons. In these embodiments, a TST-defective virus lacks its native envelope protein(s) (for instance, by gene deletion or other loss-of-function mutation of such gene(s)). Such TST-defective virus may be particularly referred to herein as a G-minus virus. Enveloped viruses that lack envelope protein(s) are not infective and can not spread from one cell to the next. Thus, as discussed above, G-minus viruses have a TST-defective phenotype.

With the envelope protein(s) (for instance, glycoprotein) gene(s) deleted from the genome of a G-minus virus, viral particles can be made that incorporate a first heterologous binding partner (such as another virus' envelope protein(s) (for instance, glycoprotein)) in their envelope (Mebatsion and Conzelmann, *Proc. Natl. Acad. Sci. USA*, 93(21):11366-70, 1996). This "pseudotyping" of the G-minus virus with the first heterologous binding partner (for instance, foreign envelope protein(s)) can be accomplished, for example, by growing the G-minus virus in cells that express the first heterologous binding partner (for instance, foreign envelope protein gene(s)). The pseudotyped G-minus virus will assemble with the first heterologous binding partner (e.g., the foreign envelope protein(s)) and, as a result, will bind to cells (for instance, primary neurons) that express a second heterologous binding partner specific for the first heterologous binding partner. Any combination of first heterologous binding partner and second heterologous binding partner can be used as long as the G-minus virus will assemble with the first heterologous binding partner in a manner whereby the first heterologous binding partner is substantially available for specific binding to its second heterologous binding partner expressed on the surface of a neuron (such as a primary neuron).

In some examples, the first heterologous binding partner is the envelope protein of a foreign (for instance, non-neurotropic or non-mammal-tropic) virus (or variant or fragment thereof that is capable of binding to its cognate receptor) and the second heterologous binding partner is the cognate receptor for the foreign envelope protein (or an envelope-protein-binding variant or fragment of such receptor). In other examples, the first heterologous binding partner is a receptor specific for the envelope protein(s) of a foreign (for instance, non-neurotropic or non-mammal-tropic) virus (or envelope-protein binding variant or fragment of such receptor) and the second heterologous binding partner is an envelope protein (or receptor-binding variant or fragment thereof) that is capable of binding to the foregoing receptor.

For certain method embodiments in which G-minus virus is a rabies virus glycoprotein deletion mutant, the first heterologous binding partner is a chimeric polypeptide that includes the intracellular (cytoplasmic) domain of the rabies virus glycoprotein and the extracellular and transmembrane domains of a non-rabies virus envelope protein.

In some instances, the foreign virus, from which a first or second heterologous binding partner (for instance, foreign envelope protein) can be derived is a retrovirus or, in more particular instances, a lentivirus (such as human immunodeficiency virus (HIV), or equine infectious anemia virus (EIAV)), or is an oncoretrovirus (such as avian sarcoma and leucosis virus (ASLV) of any subtype, such as subtype A (ASLV-A), subtype B (ASLV-B), or subtype C (ASLV-C), or murine leukemia virus (MLV)).

In particular examples, a first (or second) heterologous binding partner is one or both of HIV-1 envelope proteins gp120 and/or gp41, or a chimeric protein wherein the cytoplasmic domain of gp41 has been replaced with the cytoplasmic domain of the rabies virus glycoprotein, or a chimeric protein wherein the gp120 and gp41 proteins have been covalently linked to form a single protein. In other examples, a first (or second) heterologous binding partner is ASLV-A envelope protein, EnvA, or a chimeric envelope protein in which the cytoplasmic domain of EnvA has been replaced with the cytoplasmic domain of the rabies virus glycoprotein and the corresponding second (or first) heterologous binding protein is the cognate receptor for ASLV-A, TVA. In still other examples, a first (or second) heterologous binding partner is ASLV-B envelope protein, EnvB, or a chimeric envelope protein in which the cytoplasmic domain of EnvB has been replaced with the cytoplasmic domain of the rabies virus glycoprotein and the corresponding second (or first) heterologous binding protein is the cognate receptor for ASLV-B, TVB. In still other examples, a first (or second) heterologous binding partner is ASLV-C envelope protein, EnvC, or a chimeric envelope protein in which the cytoplasmic domain of EnvC has been replaced with the cytoplasmic domain of the rabies virus glycoprotein and the corresponding second (or first) heterologous binding protein is the cognate receptor for ASLV-C, TVC.

In examples where the first heterologous binding partner is the envelope protein(s) of a foreign virus (for instance, ASLV), the G-minus virus will have the infectious properties of the foreign virus (for instance, ASLV). If the foreign virus in question (for instance, ASLV) does not infect neurons, or mammalian cells, then the same will be true of the pseudotyped G-minus virus. Such a virus, therefore, when injected into the brain should infect substantially no neurons at all, except any that, by whatever means, have been caused to express the receptor for the foreign virus envelope protein(s) (f-EP receptor).

Figure 4:
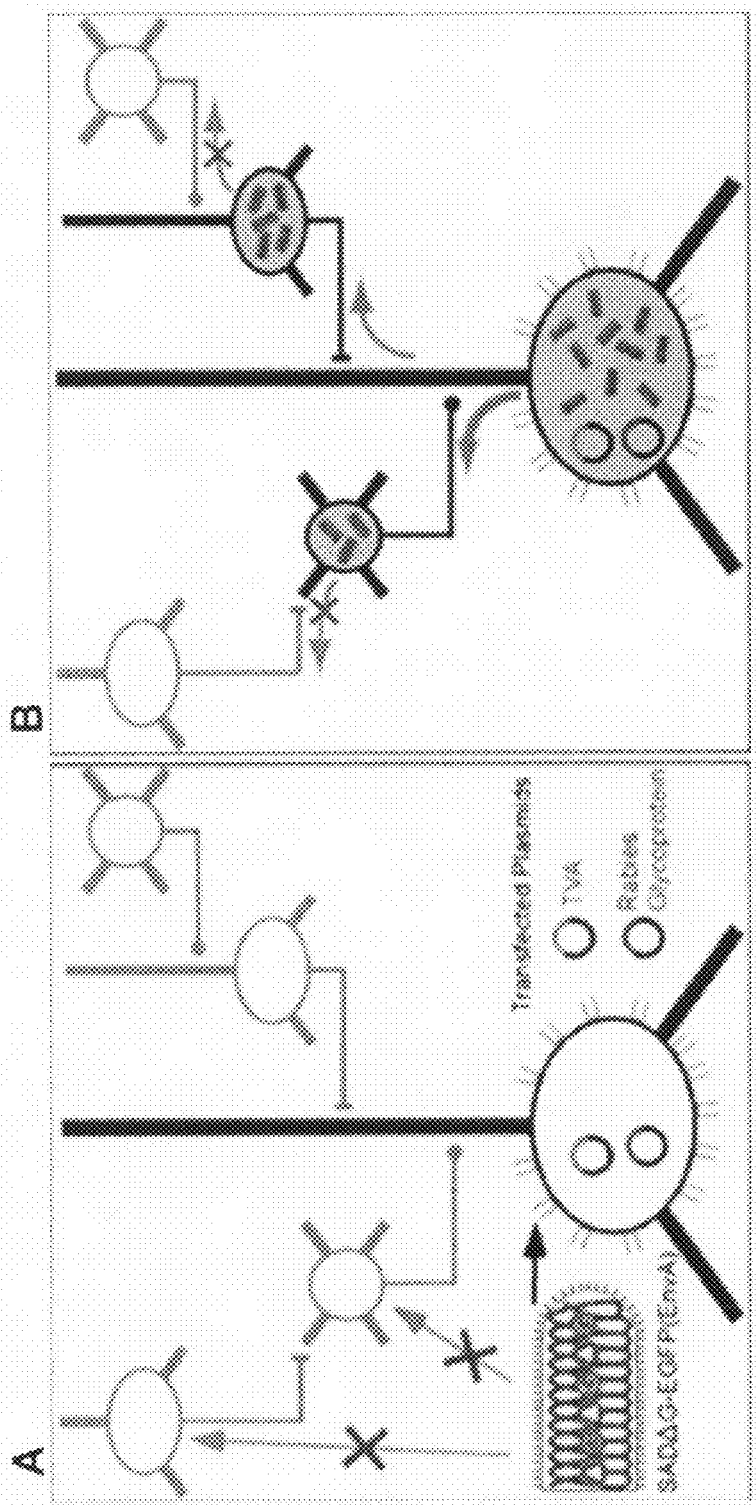
FIG. 4 is a schematic diagram illustrating an example of specific targeting and monosynaptic restriction by in situ complementation of transsynaptic tracing.

In some method embodiments, G-minus TST-defective virus is pseudotyped with one or more envelope proteins (for instance, glycoproteins) from one or more foreign viruses, and one or more receptors specific for the foreign envelope protein(s) (f-EP receptor) is (are) selectively expressed in the target primary neuron(s). The replacement foreign envelope protein(s) and f-EP receptor(s) being chosen in combination so as (i) to abolish or significantly attenuate, without further intervention, the ability of the pseudotyped TST-defective virus to infect neurons that do not express the f-EP receptor(s), and (ii) to permit the pseudotyped TST-defective virus to infect neurons that have been caused to express the f-EP receptor(s) with significantly greater efficiency than its ability to infect neurons that do not express the f-EP receptor(s). One schematic example of selective targeting of a TST-defective virus is shown in FIG. 4.

Method embodiments involving targeted delivery of a TST-defective (for instance, G-minus) virus using paired first and second heterologous binding partners (for instance, foreign envelope protein(s) and f-EP receptor(s)) also involve introduction of the second heterologous binding partner (or, more usually, expression of a nucleic acid sequence encoding the second heterologous binding partner) in to a primary neuron. A nucleic acid molecule sequence encoding a second heterologous binding partner (for instance, f-EP receptor) can be introduced into primary neuron in any manner described previously for a trans-complementing nucleic acid molecule (or trans-complementing nucleic acid sequence included therein). Preferably, an animal transgenic for the second heterologous binding partner (for instance, f-EP receptor) will have tight cell-specific control of the expression of such binding partner. In particular embodiments, a trans-complementing nucleic acid molecule includes nucleic acid sequences encoding the one or more trans-complementing polypeptides and encoding the second heterologous binding partner (for instance, f-EP receptor). In other embodiments, nucleic acid sequences encoding the one or more trans-complementing polypeptides and nucleic acid sequences encoding the second heterologous binding partner are located on separate nucleic acid molecules.

IV. Compositions and Kits

Compositions useful, at least, for performing the foregoing methods also are disclosed herein. For example, particular TST-defective viruses have not been previously contemplated by the art. These novel viruses include, without limitation, a G gene deletion mutant rabies virus including in its envelope the ASLV-A envelope protein, EnvA, the ASLV-B envelope protein, EnvB, or the ASLV-C envelope protein, EnvC, or a chimeric protein comprising EnvA, EnvB, or EnvC wherein the native cytoplasmic domain of the ASLV Env has been replaced with the cytoplasmic domain of the rabies virus glycoprotein (G protein). Any of the foregoing viruses also may include in its genome a nucleic acid sequence encoding a heterologous polypeptide, such as a detectable polypeptide (for instance, EGFP or any other fluorescent polypeptide, farnesylated EGFP or other membrane-bound form of EGFP, or a non-host polypeptide for immunohistochemical detection), a reporter of neuronal activity (for instance, calcium- or voltage-sensitive fluorophores), any polypeptide that is not itself a reporter of neuronal activity but that facilitates the use of such a reporter, polypeptide capable of mediating optical control of neuronal membrane potential (for instance, a channelrhodopsin, such as channelrhodopsin-2 or variants thereof that preserve the light sensitivity of the ion channel).

Any of the rabies virus embodiments described in this section or other TST-defective viruses described elsewhere in this disclosure can be supplied in the form of a kit useful, at least, for performing the methods described herein. In one embodiment of such a kit, an appropriate amount of a TST-defective virus is provided in one or more containers. In other embodiments, TST-defective virus may be provided suspended in an aqueous solution or as a freeze-dried or lyophilized powder, for instance. The container(s) in which the TST-defective virus is supplied can be any conventional container that is capable of holding the supplied form, for instance, microfuge tubes, ampoules, or bottles. The amount of TST-defective virus supplied can be any appropriate amount, such as $5 \times 10^8$ infectious units/ml in single use volumes of about 10 µl to about 20 µl each or in larger volumes of about 200 ml to about 500 ml from which the end user may take appropriately sized aliquots.

In other embodiments, a cell line useful for pseudotyping the TST-defective virus with a foreign virus envelope protein (for instance, ASLV EnvA, EnvB, or EnvC) may be provided in an appropriate and separate container; in some instances, such cell line will be provided in frozen form ready for expansion in culture.

Other kit embodiments will include one or more nucleic acid molecules (such as plasmids or helper virus(es)) encoding one or more trans-complementing polypeptides suitable to rescue the TST defect particular to an accompanying TST-defective virus. In more particular embodiments of this kind, the one or more nucleic acid molecules included in the kit also will encode a second heterologous binding partner (such as a f-EP receptor, for instance, TVA, TVB or TVC receptor). Such nucleic acid molecule(s) may be provided in one or more appropriate (for instance, microfuge tube) containers and in amounts suitable for transfection of neurons (for instance, in vivo, in situ (such brain slice) or in cell culture) or suitable for transformation of and expansion in bacteria or other carrier. The nature and number of nucleic acid molecules useful for trans complementation of a TST defect and, optionally, for the expression of second heterologous binding partner (such as a f-EP receptor) have been described elsewhere in this disclosure and are equally applicable to kit embodiments.

Some kit embodiments may include an animal transgenic for one or more genes encoding polypeptides necessary to complement the TST defect of a TST-defective virus also provided with the kit. In some such embodiments, the transgenic animal may express the trans-complementing polypeptides in a tissue-specific manner, for instance, predominately in neurons or in particular types of neurons. In other kit embodiments, an animal transgenic for one or more genes encoding a second heterologous binding partner (such as a f-EP receptor, for instance, TVA, TVB or TVC receptor) may be included. In some such embodiments, the transgenic animal may express the one or more genes encoding a second heterologous binding partner in a tissue-specific manner, for instance, predominately in neurons or in particular types of neurons.

In one embodiment, a kit includes instructional materials disclosing means of use of a TST-defective virus and, optionally, a packaging cell line, and/or one or more nucleic acid molecules (such as trans-complementing nucleic acid molecules and/or nucleic acid molecule(s) encoding a second heterologous binding partner, such as a f-EP receptor) in a disclosed method. The instructional materials may be written, in an electronic form (for instance, computer diskette or compact disk) or may be visual (for instance, video files). The kits may also include additional components to facilitate the particular application for which the kit is designed. Thus, for example, the kit may additionally contain means of detecting a label (for instance, enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

The following examples are provided to illustrate certain particular features and/or embodiments. These examples should not be construed to limit the disclosure to the particular features or embodiments described.

Example 1

Construction and Function of a Rabies Virus Glycoprotein Deletion Mutant that Encodes a Marker Gene Rabies virus is a neurotropic virus that infects neurons via axon terminals, replicates in the cytoplasm, and spreads between synaptically coupled neurons in an exclusively retrograde direction. A single infectious unit of rabies virus introduced into a brain is sufficient to cause a full-scale case of rabies (Lafay et al., *Virol.*, 183(1):320-30, 1991, Ito et al., *J. Virol.*, 75(19):9121-9128, 2001).

Mebatsion et al. (*Cell*, 84(6)941-51, 1996) previously described a rabies virus with the envelope glycoprotein gene deleted from its genome (G⁻ rabies virus). The G⁻ rabies virus was grown in cells where the glycoprotein was provided in trans for incorporation into the viral particles' membranes. The G⁻ rabies virus normally infected neurons with which it came in contact. Because the glycoprotein plays no role in transcription and replication, the G⁻ rabies virus replicated its viral core within initially infected cells; however, with no means of synthesizing glycoprotein, the newly created progeny did not substantially bud out through the host cell membrane into the extracellular space. The few that managed to do so were "sterile", unable to bind to glycoprotein receptors on the presynaptic cells and penetrate them to begin a new round of infection (Mebatsion et al., *Cell*, 84(6)941-51, 1996; Etessami et al., *J. Gen. Virol.*, 81(9):2147-2153, 2000). Deleting the glycoprotein gene, therefore, constituted a block to neuron-to-neuron transfer of rabies virus. Exemplary methods for producing rabies virus constructs and particular rabies virus constructs are described in U.S. Pat. Nos. 6,033,886 and 6,719,981 (hereby incorporated by reference in their entirety).

This Example describes the construction of a G⁻ rabies virus, referred to as SADΔG-EGFP, which has introduced into its genome a gene encoding enhanced green fluorescent protein (EGFP). The SADΔG-EGFP virus replicated to high copy number and expressed high levels of EGFP in single neurons, but was unable to spread beyond the first-infected cell (as shown schematically in FIGS. 2B and 2C).

A. Construction of pSADΔG-EGFP

The pSADΔG-EGFP cDNA plasmid was constructed by replacement of the G-gene of pSAD L16 (Schnell et al., *EMBO J.*, 13(18):4195-4203, 1994) with the EGFP reporter gene (Clontech), resulting in the genome organization 3'-N-P-M-EGFP-L-5' (see FIG. 2B).

A G deletion clone was generated from the rabies virus full-length cDNA clone pSAD L16 (Schnell et al., *EMBO J.*, 13:4195-4203, 1994). To create unique restriction sites allowing the replacement of the G open reading frame (ORF) without destroying the transcription signals of the G gene, site-directed mutagenesis was applied to introduce a single PpuMI site (at residue 3303 of the rabies virus antigenome, GenBank Accession No. M31046; Conzelmann et al., *Virol.*, 175:485-499, 1990) located downstream of the transcription start signal (residue 3290 of GenBank Accession No. M31046) and an NheI site (at residue 5335) upstream of the transcriptional stop/polyadenylation signal (residue 5359 of GenBank Accession No. M31046) using the following primers:

```
                                         (SEQ ID NO: 5)
5'-ACTATTAACATCCCTCAAAgGACcCAAGGAAAGATGGTTCCTC-3'
and
                                         (SEQ ID NO: 6)
5'-TTTTCTCGACTGAAAAGCTagcATGACCCAGCACTTTATAA-3'
``` with the restriction sites introduced underlined and the changed nucleotides in lower case letters. The intervening sequence was removed from the full length clone by PpuMI/NheI digestion, fill up by Klenow enzyme, and religation, resulting in the reconstitution of both PpuMI and NheI sites in the plasmid pSADΔG Ppu. The EGFP ORF was cut out from pEGFP-N3 (Clontech) by SmaI and NotI, and the fragment was ligated into PpuI-digested pSADΔG Ppu after fill-in with Klenow enzyme. Transcription of the novel EGFP mRNA would therefore be directed by the authentic G gene transcription signals. The sequences flanking the G region in the original and modified plasmids were as follows, with transcription start and stop/polyadenylation signals underlined, ORF sequences shown in bold with translation initiation and termination codons underlined, and nucleotides constituting (or derived from) the PpuMI recognition site in italics:

pSAD L16, G start:

```
                                         (SEQ ID NO: 7)
TTAACATCCCTCAAAAGACTCAAGGAAAGATGGTTCCTCAGGTCCT;

pSAD L16, G stop:
                                         (SEQ ID NO: 8)
AGACTGTAAGGACTGGCCGTCCTTTCAACGATCCAAGTCCTGAAGATCAC

CTCCCCTTGGGGGGTTCTTTTTGAAAAACCTGGGTTCAATAGTCCTCCTT

GAACTCCATGCAACTGGGTAGATTCAAGAGTCATGAGATTTTCATTAATC

CTCTCAGTTGATCAAGCAAGATCATGTCGATTCTCATAATAGGGGAGATC

TTCTAGCAGTTTCAGTGACTAACGGTACTTTCATTCTCCAGGAACTGACA

CCAACAGTTGTAGACAAACCACGGGGTGTCTCGGGTGACTCTGTGCTTGG

GCACAGACAAAGGTCATGGTGTGTTCCATGATAGCGGACTCAGGATGAGT

TAATTGAGAGAGGCAGTCTTCCTCCCGTGAAGGACATAAGCAGTAGCTCA

CAATCATCTCGCGTCTCAGCAAAGTGTGCATAATTATAAAGTGCTGGGTC

ATCTAAGCTTTTCAGTCGAGAAAAAAA;

pSADΔG Ppu start/stop:
                                         (SEQ ID NO: 9)
TTAACATCCCTCAAAGGACCCGCTAGCTTTTCAGTCGAGAAAAAAA;
```

-continued pSADΔG-EGFP, EGFP start:
(SEQ ID NO: 10)
TT<u>AACATCCCT</u>CAAAGGACGGGATCCATCGCCACC<u>ATG</u>GTGAGCAA;
and pSADΔG-EGFP, EGFP stop:
(SEQ ID NO: 11)
T<u>ACAAG</u><u>TAA</u>AGCGGCCGACCCGCTAGCTTTTCAGTCG<u>AGAAAAAAA</u>.

The cDNA construct pSADΔG-EGFP was rescued into viral cores in cells expressing rabies virus N, P, and L proteins from transfected plasmids as described previously (Finke and Conzelmann, *J. Virol.*, 73(5):3818-3825, 1999). After 3 days of incubation, the cells were repeatedly transfected with G-encoding pTIT-G plasmid (5 µg cDNA/$10^6$ cells) until spread of virus was detectable by EGFP expression. The virus-containing cells were trypsinized and mixed with a hygromycin-resistant BSR cell line expressing rabies virus G and M proteins after induction with doxycyclin (clone MG139) (Finke and Conzelmann, *J. Virol.*, 77(22):12074-12082, 2003). Two days after cell mixing, BSR T7/5 cells were eliminated by adding hygromycin at 1 mg/ml. Expression of rabies virus G protein in MG139 cells was repeatedly induced until approximately 50% of the cell culture was fluorescent. Supernatants were transferred to fresh MG139 cells for SADΔG-EGFP stock production.

SADΔG-EGFP virus stocks were clarified from cell debris by low speed centrifugation, and the viruses were purified by centrifugation in an SW 28 rotor (27,000 rpm, 2 hrs, 4° C.) through 20% sucrose onto a 60% sucrose cushion prepared in TEN buffer (10 mM Tris (pH 7.4), 50 mM NaCl, 1 mM EDTA). The purified viruses were collected from the top of the 60% sucrose layer.

Virus titer was determined in triplicate by serial dilution and overnight infection of HEK-293T cells followed by fluorescence activated cell sorting on a FACSCAN™ (BD Biosciences, San Jose, Calif.) three days later.

B. Stereotaxic Injection of SADΔG-EGFP into Mouse Brain

The SADΔG-EGFP virus was stereotaxically injected into mouse brain. C57B/6 mice were anesthetized with ketamine (100 mg/kg IM) and xylazine (10 mg/kg IM). Long-Evans rats were anesthetized with ketamine (100 mg/kg IM), xylazine (5 mg/kg IM), and acepromazine (1 mg/kg IM). Virus was loaded into pulled glass pipettes (tip inner diameter of 30-50 µm) and injected using a Picospritzer III (Parker Hannifin/General Valve Corporation, Fairfield, N.J.) at approximately 20 nl/min. For targeting injections to thalamus, stereotaxic coordinates, in millimeters relative to bregma, were −3.6 AP, +2.4 AP, −5.8 DV (rat), for slice physiology studies; and −1.82 AP, +1.25 LM, −3.5 DV for neuronal survival time course study.

For anatomical studies, animals were deeply anesthetized 2-34 days postinjection with 4% isoflurane and perfused transcardially with 4% paraformaldehyde in PBS. Brains were postfixed and cryopreserved overnight in 4% paraformaldehyde/30% sucrose in PBS, then kept in 30% sucrose in PBS until sectioning. Brains were sectioned on a freezing microtome at 50-80 µm, and then stored in 30% ethylene glycol/30% glycerol/40% PBS at −20° C. Immunostaining was with a chicken anti-GFP polyclonal antibody (Aves, 1:500) and either Cy2-conjugated donkey anti-chicken polyclonal antibody (Jackson ImmunoResearch, 1:100) or AlexaFluor 555-conjugated goat anti-chicken antibody (Invitrogen, 1:100).

Six days following injection in the thalamus, neurons and glia at the injection site were illuminated with large amounts of EGFP. On the other hand, substantially no EGFP fluorescence was observed in control tissue from brains of mice that received either sham injections or no injection. Large numbers of cell bodies in regions of the brain that project axons to the thalamic injection site were similarly labeled presumably because the virus infected the cell at an axonal projection near the injection site. Numerous pyramidal cells in the deep layers of ipsilateral cortex were retrogradely labeled. Of cortical cells, only layer 5 and layer 6 pyramidal cells, which provide the sole cortical projections to thalamus (Deschenes et al., *Brain Res. Brain Res. Rev.*, 28(3):286-308, 1998; Killackey and Sherman, *J. Neurosci.*, 23(19):7381-7384, 2003), were infected.

Infected cells invariably displayed uniform fluorescence filling of all of their processes. The EGFP labeling was visible at 2 days postinjection, increased steadily thereafter, and reached maximum intensity by approximately 7 days postinjection. Similar results were obtained from injections in striatum, superior colliculus, and various cortical areas.

C. SADΔG-EGFP Did not Substantially Affect the Electrophysiological Properties of Infected Neurons and Was Noncytotoxic for an Extended Period Whole-cell recordings were made from fluorescent cortical cells in brain slices prepared from rats injected with SADΔG-EGFP into thalamus 5-12 days previously. Vibratome-cut 400 µm thick brain slices were prepared. Slices were cut in ice-cold artificial cerebrospinal fluid (ACSF) (124 mM NaCl, 5 mM KCl, 2.5 mM $CaCl_2$, 1.3 mM $MgSO_4$, 1 mM $H_2PO_4$, 26 mM $NaHCO_3$, and 11 mM dextrose) and maintained afterward submerged in room temperature ACSF aerated with 95% oxygen/5% $CO_2$ for at least one hour, then transferred to a recording chamber, continually perfused with aerated room temperature ACSF, mounted on an infrared DIC microscope (Olympus). Glass recording electrodes (8-12 MΩ resistance) were filled with intracellular solution (140 mM potassium gluconate, 8 mM NaCl, 10 mM HEPES, 1.3 mM EGTA, 2 mM ATP, and 0.3 mM GTP, adjusted to pH 7.7 with KOH).

There were no significant differences in the gross electrophysiological properties of infected cells versus those of nearby nonfluorescent cells. The resting membrane potential of infected cells was −49.6±8.0 mV (mean±SD; n=14) while that of noninfected cells (n=9) was −50.7±6.0 mV. Action potential thresholds were −36.4±9.2 mV and −39.3±10.1 for the infected and control cells, respectively (p=0.73 and 0.48, respectively; two-tailed Student's t-tests). Thus, infection with SADΔG-EGFP does not affect the gross membrane properties of infected cells up to 12 days postinfection.

To estimate the time course of survival for neurons infected with SADΔG-EGFP, mouse thalami were injected with virus solution and sacrificed at 2 day intervals postinjection to count fluorescent cells in overlying cortex. The number of extant fluorescent cells remained roughly constant up to approximately 16 days and then dropped to a lower but persistent number. This dropoff was accompanied by morphological changes in many surviving neurons, such as blebbing of processes and the appearance of "bifurcating" somata.

D. SADΔG-EGFP Provided Better Labeling of Neurons as Compared to Adenovirus or Pseudorabies Virus Other viruses are known to infect retrogradely, including pseudorabies, adenovirus, alpha-herpesviruses and lentiviral vectors pseudotyped with envelope glycoproteins of various strains of rabies virus (Maskos et al., *Proc. Natl. Acad. Sci. USA*, 99(15):10120-5, 2002; Zou et al., *Nature*, 414(6860): 173-9, 2001; Norgren and Lehman, *Neurosci. Biobehav. Rev.*, 22(6):695-708, 1998; Lafay et al., *Virology*, 183(1):320-30, 1991; Ito et al., *J. Virol.*, 75(19):9121-8, 2001; Mebatsion et al., *Cell*, 84(6):941-51, 1996). Therefore, such viruses can be used in place of rabies virus.

SADΔG-EGFP was compared with either adenovirus E1-E2-E3 deletion mutant or pseudorabies virus thymidine kinase deletion mutant encoding EGFP driven by the synapsin or human cytomegalovirus (HCMV) promoters, respectively. Both the number of retrogradely infected cells and the intensity of fluorescence in infected cells were higher with the SADΔG-EGFP as compared to either the adenovirus or pseudorabies virus construct.

Collectively, this Example demonstrates that SADΔG-EGFP virus was efficiently taken up by neurons in a retrograde fashion, brightly labeled the cells, labeled fine details of both axonal and dendritic arbors, and was substantially non-cytotoxic to the label cells for an extended period. Moreover, due to its lack of the gene encoding glycoprotein, SADΔG-EGFP was unable to label cells other than those into which the viral construct was introduced (as shown schematically in FIG. 2C) (see also Wickersham et al., *Nat. Methods*, 4(1):47-49, 2007)

Example 2

Specific Targeting of and Monosynaptic Labeling by a Rabies Virus Glycoprotein Deletion Mutant This Example provides a representative method involving a rabies virus monosynaptic tracer, which tracer can be specifically targeted to a particular population of originating neurons and is transmitted substantially only to neurons monosynaptically connected to the originating neurons. Although this example describes a tracer that includes the envelope protein of the ASLV-A virus (EnvA), one skilled in the art will appreciate that other envelope proteins can be used (such as EnvB), and that other viruses can be used in place of the rabies virus.

The interaction between subgroup A avian sarcoma and leukosis virus (ASLV-A) and its receptor(s) is highly specific. The envelope protein of the ASLV-A virus (EnvA) can direct virus infection specifically into cells that express the cognate TVA viral receptor (Young et al., *J. Virol.*, 67(4):1811-6, 1993; Bates et al., *Cell*, 74(6):1043-51, 1993; Barnard et al., *Virology*, 344(1):25-9, 2006), a protein which is found in birds but not mammals (Young et al., *J. Virol.*, 67:1811-6, 1993; Bates et al., *Cell*, 74:1043-51, 1993; Federspiel et al., *Proc. Natl. Acad. Sci. USA*, 91:11241-5, 1994; Barnard et al., *Virology*, 344:25-9, 2006). The EnvA-TVA viral receptor interaction was used in this Example to target initial infection to a genetically defined population of originating neurons (see schematic illustration in FIG. 4).

Briefly, the rabies virus-EGFP construct, SADΔG-EGFP, described in Example 1 was pseudotyped with a chimeric glycoprotein consisting of the extracellular and transmembrane domains of EnvA fused to the intracellular domain of rabies virus G protein to produce the virus referred to as SADΔG-EGFP(EnvA). Infection by SADΔG-EGFP(EnvA) was restricted to only a small subpopulation of neuronal cells that were engineer to express TVA (see, for instance, the neuron indicated by the dotted line in FIGS. 5B and 5C). By supplying the rabies virus G gene in trans within these initially infected cells, rabies virus then was able to assemble and be retrogradely transported to pre-synaptic cells; however, because the viral glycoprotein gene is not present in the transsynaptically infected cells, the virus cannot spread any further (see schematic examples in FIGS. 3 and 4). Therefore, this system provides for the unambiguous identification of neurons monosynaptically connected to genetically defined neurons of origin.

Small numbers of relatively isolated neurons present in cultured slices of neonatal rat brain were transfected, using the "gene gun" (Bio-rad, Hercules, Calif.), with plasmid DNA encoding TVA, rabies virus G, and DsRed2 to label the transfected cell population. A day after transfection, SADΔG-EGFP(EnvA) was added to the culture wells, and virus infection was subsequently monitored using fluorescence microscopy to score EGFP expression.

In six slices quantitatively examined six days postinfection, 242 cells were identified that expressed DsRed2 (red), 62 of which also expressed EGFP (green). Spectacularly, the double-labeled cells were surrounded by large clusters of virus-infected neurons (totaling 5,424) expressing only EGFP (see, for instance, FIG. 5C). Qualitatively similar results were obtained with dozens of other brain slices tested. It is believed that the red and green TVA-expressing cells at the centers of these clusters were initially infected by the EnvA-pseudotyped virus and the additional thousands of green cells were connected directly to the initially infected ones.

To illustrate the specificity of infection with EnvA pseudotyped virus and the requirement of G expression for viral spread, virus infection was also conducted with brain slices that either were not transfected or were transfected with plasmid DNA encoding TVA and DsRed2 (but not rabies virus G). Consistent with the low level tropism of ASLV-A for mammalian cells, examination of 20 independent untransfected brain slices led to the identification of only a single EGFP-expressing cell. Another set of 12 slice cultures was transfected with plasmid DNA encoding TVA and DsRed2, but not rabies virus G. A day after transfection, SADΔG-EGFP (EnvA) was added to the culture wells, and virus infection was again monitored using fluorescence microscopy to score EGFP expression. In 12 slices, 43 cells expressed DsRed2; 23 of these red cells, and again only one untransfected cell, also expressed EGFP. Thus, in the absence of the rabies virus glycoprotein gene, virus infection was restricted almost entirely to the TVA-expressing cells and did not spread beyond the initially infected cells.

This Example demonstrates that in situ complementation of the G gene deletion mutant rabies virus worked extremely effectively. The initial virus infection was restricted to TVA-positive cells, complementation with rabies virus G was necessary for spread beyond these cells, and this complementation was sufficient to unleash a viral infection from these cells to thousands of others surrounding them in the slices.

Figure 5:
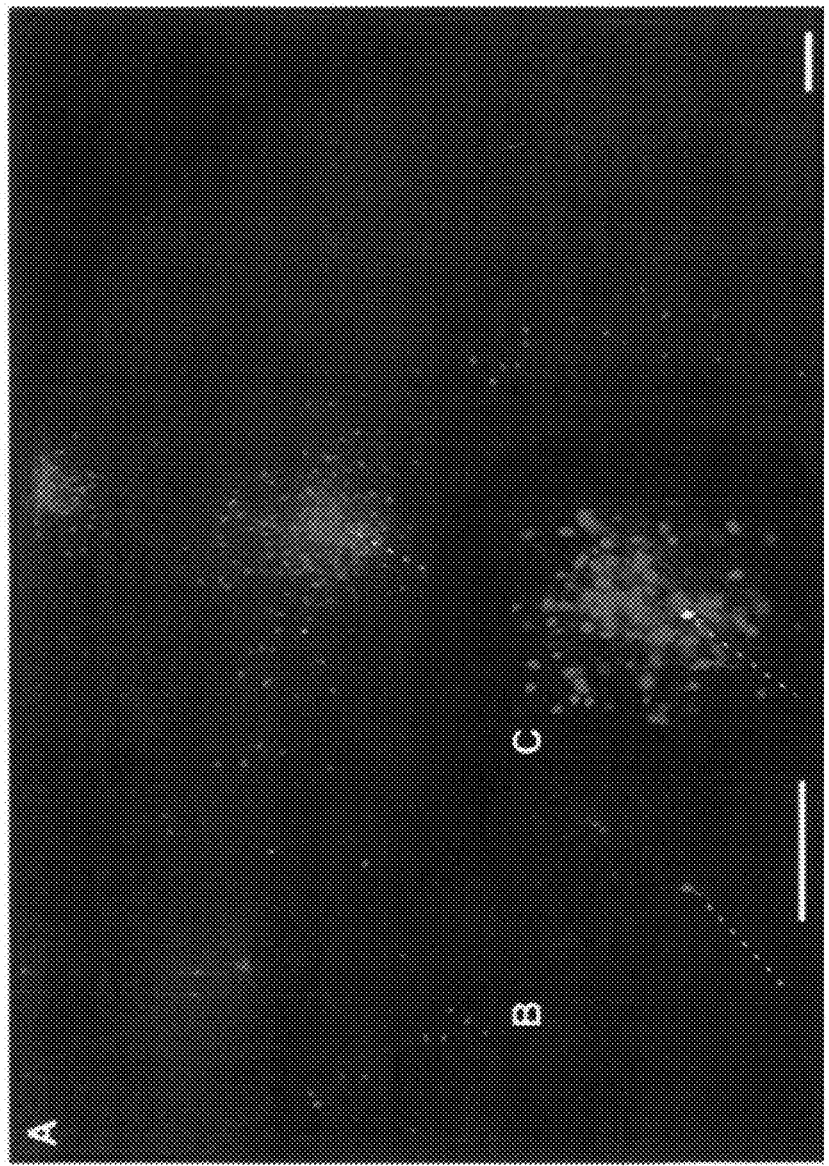
FIG. 5 shows a series of digital fluorescence micrographs.

This Example also demonstrates that the complemented virus was quite capable of spreading from a single starting neuron to a vast number of neighboring neurons. Due to the manner in which the gene gun operates, it was not feasible in this Example to transfect one neuron or fewer per slice. Nevertheless, in many cases, clusters of secondarily infected neurons were clearly centered on a single DsRed2-expressing cell, as seen in FIG. 5. Cells expressing both DsRed2 and EGFP, which were at the center of EGFP-positive cell clusters, included those with morphologies of both inhibitory and excitatory neurons, indicating that the complemented rabies virus can efficiently spread from either cell type.

Example 3

Monosynaptically Labeled Cells are Functionally Connected

This Example demonstrates that neurons labeled as described in Example 3 are functionally connected. Thus, the observed labeling was substantially transsynaptic and not, for instance, nonspecific infection of neighboring cells.

Figure 6:
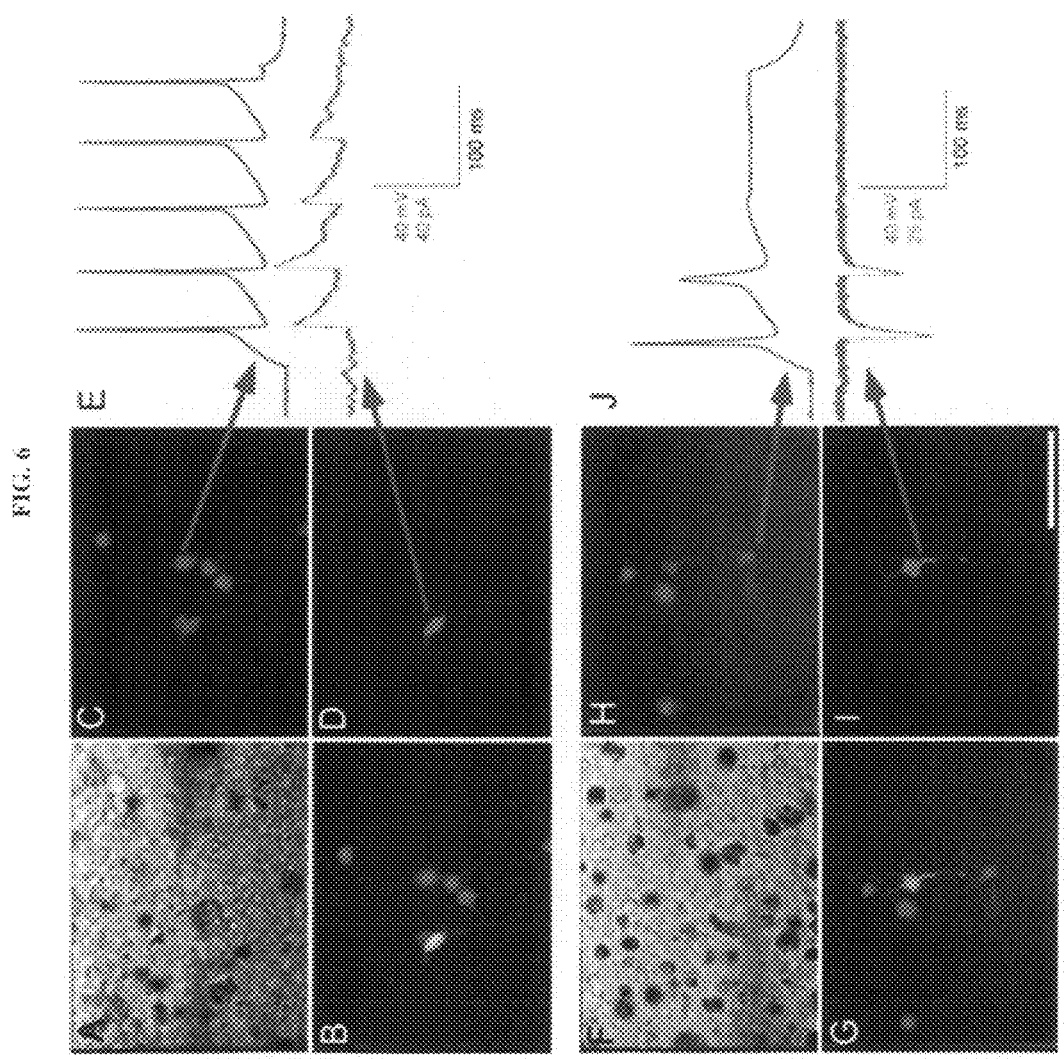
FIG. 6 shows a series of fluorescent or infrared differential interference contrast (DIC) digital micrographs together with tracings of intracellular recordings from neurons shown in the micrographs. Collectively, these results illustrate that SADΔG-EGFP(EnvA) viral spread was specific to cells presynaptic to the initially infected cell.

Paired whole-cell recordings were made from putatively pre- and postsynaptic cells. Cells fluorescent in both red and green channels (red/green cells) were recorded under voltage clamp while nearby green-only cells, held in current clamp, were depolarized to fire action potentials (see, for instance, FIGS. 6A-D and F-I). Synaptic currents in the voltage-clamped red/green cell that were simultaneous with the green cell's action potentials indicated a monosynaptic connection as seen in the example traces in FIGS. 6E and 6J. Non-fluorescent cells at similar distances from the red/green cells were also stimulated as controls. Because the gene gun typically transfected many more than one neuron within a slice, recording were made only from red/green cells with no other red/green cells present within 250 microns. Of eleven green cells, nine were found to be directly connected to their nearby red/green putatively postsynaptic partners. Of these nine connected pairs, 5 elicited excitatory currents (for instance, FIG. 6J), while 4 elicited inhibitory currents (for instance, FIG. 6E). By contrast, nine control pairs, each consisting of a non-fluorescent neuron near a red/green cell, were recorded, and none was found to be connected.

Because, as seen in FIG. 5A, a single postsynaptic cell labeled cells across hundreds of microns, it is believed that the two infected cells that were not found to be connected to the recorded transfected cells were connected to some other transfected cell elsewhere in the slice. Fundamentally, there is no reason for the spread of the in situ complemented virus to be any less synaptically specific than that of replication-competent rabies virus, which available evidence indicates to be highly specific (Ugolini et al., *J. Comp. Neurol.*, 356:457-80, 1995; Kelly & Strick, *J. Neurosci. Methods*, 103:63-71, 2000).

This Example illustrates that a monosynaptic tracing virus can spread effectively from individual originating neurons to neurons with which the originating cell is functionally connected, for instance, a functional synapse.

Example 4

Representative Materials and Methods

This Example describes materials and methods used in Examples 2-3.

A. Production of Packaging Cell Line

The extracellular and transmembrane domains of the ASLV-A envelope protein were amplified from the plasmid pAB6 (Boerger et al., *Proc. Natl. Acad. Sci. USA*, 96(17): 9867-72, 1999) using the following primers: TTTCA GCGGCCGCATGGAAGCCGTCATAAAGGC forward (NotI site underlined; SEQ ID NO: 1) and AGGTTCTGATCGATTGACTCTTCTGCAAGGCAGGC ACACTACTAGC reverse (homology with rabies virus glycoprotein gene underlined; SEQ ID NO: 2). ACCUPRIME™ Pfx (Invitrogen, Carlsbad, Calif.) was used for all PCR reactions. The cytoplasmic domain region of the SAD B19 glycoprotein gene was amplified from pHCMV-RabiesG (Sena-Esteves et al., *J. Virol. Methods*, 122(2): 131-9, 2004) using primers GCTAGTAGTGTGCCTGCCTTGCAGAAGAGT CAATCGATCAGAACCT forward (homology with TVA800 gene underlined; SEQ ID NO: 3) and GACGGC GGATCCTCACAGTCTGGTCTCACCCCCAC reverse (NotI site underlined; SEQ ID NO: 4). The resulting products were then combined in a third reaction using the first and last primers listed above, producing a chimeric gene was cloned into the NotI and BamHI sites of the murine leukemia virus (MLV) transfer vector pCMMP-IRES-GFP (Melikyan et al., *J. Virol.*, 78(7):3753-62, 2004). The insert region of the final cloning product, termed pCMMP-EnvARGCD-IRES-GFP, was verified by sequencing.

VSV-pseudotyped MLV was then produced as described (Melikyan et al., *J. Virol.*, 78(7):3753-62, 2004). Briefly, 293T cells (ATCC, Manassas, Va.) were transfected with LIPOFECTAMINE™ 2000 (Invitrogen, Carlsbad, Calif.) according to the manufacturer's protocol using the following DNA quantities in a 10 cm plate: transfer vector, 2.5 µg; MLV packaging construct pMD.old.gagpol, 2.5 µg; and VSV glycoprotein expression vector pMD.G, 3 µg. Supernatants were collected 48 and 72 hours posttransfection, pooled, filter sterilized and pelleted by ultracentrifugation for 1 hour at 111,000×g. Pellets were resuspended in 1 ml medium and applied after titering to BHK-21 cells (ATCC) at an MOI of approximately 4 overnight. After four passages, cells were sorted for high EGFP fluorescence with a FACSDIVA™ (BD Biosciences, San Jose, Calif.). The resulting cell line was termed BHK-EnvARGCD.

B. Production of Virus

BHK-EnvARGCD cells were plated in 12 well plates at $2 \times 10^5$ cells/well. The following day, the glycoprotein-gene-deleted rabies virus SADΔG-EGFP (see Example 1) was added at an MOI of 1.5. One day later, the cells in each well were trypsinized and re-plated into a 10 cm plate. Virus-containing supernatants were harvested two days later, filter sterilized and frozen at −80° C. in 1 ml aliquots.

Virus titers were determined by serial dilution and overnight infection of 293T-TVA800 cells (Narayan et al., *J. Virol.*, 77(3):1977-83, 2003) and 293T cells followed by fluorescence activated cell sorting on a FACSCAN™ (BD Biosciences) 3 days later. Data were subsequently analyzed with CELLQUEST™ software (BD Biosciences) to determine the fraction of fluorescent cells and the titer taken as $\mu \ln(1-p) * N_o / v$, where p is the fraction of fluorescent cells, $N_o$ is the number of cells at infection, and v is the volume of applied virus.

C. Transfection and Infection

Brain slices were prepared from the cortex of 3-7-day-old rats as described previously for ferrets (McAllister et al., *Neuron*, 15:791-803, 1995; Dantzker & Callaway, *J. Neurosci.*, 18:4145-54, 1998). Briefly, animals were deeply anesthetized with sodium pentobarbitol (100 mg/kg, i.p.) and decapitated. Brains were extracted under sterile conditions and submerged in 4° C. HEPES-buffered artificial CSF (ACSF) (in mM): 140 NaCl, 5 KCl, 1 MgCl$_2$, 24 dextrose, 10 HEPES, and 1 CaCl$_2$, pH 7.4. The cortex was cut into 400 µm parasagittal slices using a tissue slicer (Katz, *J. Neurosci.*, 7(4): 1223-49, 1987). Slices were then transferred onto cell-culture inserts (0.4 µm pore size; Falcon, Franklin Lakes, N.J.) in six well culture dishes and fed with medium from below. The medium was composed of 50% basal Eagle's medium without glutamine, 25% HBSS, 330 mM dextrose, 10 mM HEPES, 200 mM L-glutamine, 10 U/ml penicillin-streptomycin (all from Invitrogen, San Diego, Calif.), and 25% horse serum (Hyclone, Logan, Utah).

One day following slice preparation, slices were transfected using the HELIOS™ Gene Gun (Bio-Rad, Hercules, Calif.) according to the manufacturer's instructions. Briefly, gold microcarriers (1.6 μm diameter; Bio-Rad) were coated with vector DNA at a concentration of 60 μg of DNA per 12.5 mg of gold and shot into the slices at 90-100 psi. The following plasmids were used: Controls: pCAG-DsRed2, 5 μg; pCMMP-TVA800 (Narayan et al., *J. Virol.*, 77(3):1977-83, 2003), 30 μg. Experimental: pCAG-DsRed2, 5 μg; pCMMP-TVA800, 30 μg, pHCMV-RabiesG (Sena-Esteves et al., *J. Virol. Methods*, 122(2): 131-9, 2004), 15 μg. All transgenes were expressed under the control of the human cytomegalovirus (CMV) immediate-early promoter except for DsRed2, which was driven by the CAG hybrid promoter (Niwa et al., *Gene*, 108(2):193-9, 1991; Borrell et al., *J. Neurosci. Methods*, 143(2):151-8, 2005). One day following transfection, 50-100 μl of virus stock solution ($7.8 \times 10^4$ pfu/ml) was applied to the surface of each slice.

D. Electrophysiological Recordings

Three (3) to 9 days following application of virus, slices were transferred to recording chambers perfused with room temperature artificial cerebral spinal fluid (ACSF), composition in mM: 124 NaCl, 5 KCl, 1.25 $KH_2PO_4$, 1.3 $MgSO_4$, 3.2 $CaCl_2$, 26 $NaHCO_3$ and 10 glucose. Glass recording electrodes (7-10 MΩ resistance) filled with an intracellular solution consisting of 130 mM potassium gluconate, 6 mM KCl, 2 mM $MgCl_2$, 0.2 mM EGTA, 10 mM HEPES, 2.5 mM $Na_2ATP$, 0.5 mM $Na_2GTP$, 10 mM potassium phosphocreatine and 0.3% biocytin, adjusted to pH 7.25 with KOH, were used for whole-cell current-clamp recordings. Cells were targeted using fluorescence and DIC optics. Putatively presynaptic cells were current clamped while postsynaptic ones were voltage clamped at −65 mV to detect EPSCs and −30 mV for IPSCs.

Example 5

Helper Viruses that Allow the Identification of Neurons Providing Direct Synaptic Input to Specific Cell Types This Example describes a method of using the tracing methods described above that employs helper viruses that allow the identification of neurons providing direct synaptic input to specific cell types. In certain embodiments, helper viruses efficiently infect neurons through their axonal terminal fields and result in the expression of, for instance, rabies glycoprotein (RG) and a marker protein. When combined with infection with AG-GFP rabies virus (SADΔG-EGFP, see Example 1), this results in transsynaptic spread and labeling of neurons that are directly presynaptic to specific types of projection neurons. Exemplary helper viruses include, in certain embodiments, adenovirus, HSV amplicon vectors, and lentivirus pseudotyped with the RG.

A. Retrogradely-Infecting Helper Viruses.

Gene expression can be targeted to specific cell types by using a viral vector that efficiently infects neurons via their distant axon terminals (Callaway, *Trends Neurosci.* 2005; 28(4):196-201). This allows gene expression within complex neuropil to be restricted to those neurons that send an axon to a particular distant target, without expression in neighboring neurons that do not project to that target. Viral vectors that infect retrogradely and yield stable long-term gene expression without apparent toxicity include RG-pseudotyped lentivirus, HSV amplicon vectors, and adenoviral vectors (Mazarakis et al., *Hum. Mol. Genet.* 2001; 10(19):2109-2121; Wong et al., *Mol. Ther.* 2004; 9(1): 101-111; Tomioka et al., *J. Histochem. Cytochem.* 2006; 54(5):539-548; Sandler et al., *J. Neurosci. Methods* 2002; 121(2):211-219).

Figure 7:
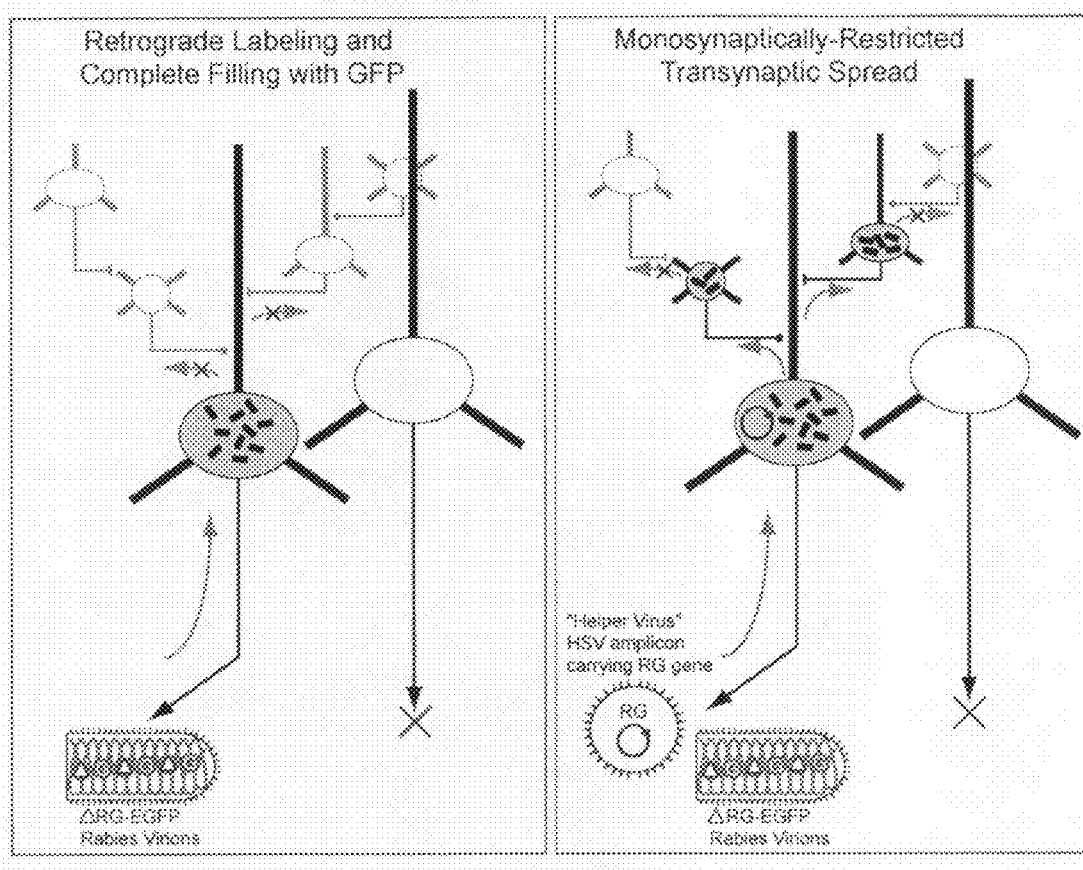
FIG. 7 shows retrograde labeling (left) and monosynaptically restricted transsynaptic labeling (right) with ΔRG-EGFP rabies virus. As illustrated in the left panel, when ΔRG-EGFP rabies is injected alone into a particular brain region it infects neurons with axon terminals in that region. The viral particles are transported back to the cell body where they can replicate and drive expression of EGFP, resulting in complete filling of axons and dendrites. Because the RG gene has been deleted from the viral genome, the viral particles produced in the infected cells lack RG on their envelope and therefore cannot spread beyond the initially infected projection neurons. The right panel illustrates a method for obtaining monosynaptically-restricted, retrograde transsynaptic spread of ΔRG-EGFP in which ΔRG-EGFP is co-injected along with a helper virus, for example, an HSV amplicon vector that carries the RG gene. The helper virus, like ΔRG-EGFP, also efficiently infects neurons via their axon terminals and delivers its genetic payload to the cell body. In this case, however, the virus does not replicate, it simply allows expression of the gene it carries. Because the helper virus carries the RG gene, RG is expressed in the infected cells. This is packaged onto the ΔRG-EGFP rabies virions, allowing them to spread transsynaptically in the retrograde direction, to infect neurons that are directly presynaptic to the initially infected projection neurons. But the virus cannot spread beyond these secondarily infected neurons because they do not express RG.

The strategy for labeling the neurons that are directly presynaptic to neurons projecting to a particular distant target is illustrated in FIG. 7. Specific types of projection neurons were targeted by co-injection of AG-GFP rabies virus and a helper virus that also infects retrogradely and expresses RG. Complementation with RG expressed from the helper virus allowed the AG-rabies virus to spread retrogradely to neurons directly presynaptic to the projection neurons.

In one example, the helper virus was an RG-pseudotyped lentivirus that expresses both RG and a nuclear-localized (histone-tagged) GFP, although other non-lentiviral enveloped viruses that are pseudotyped, for instance with the vesicular stomatitis virus (VSV), also could be used. One skilled in the art will recognize that certain enveloped viruses, such as HSV and PRV, are already retrogradely infectious due to the actions of their native glycoproteins, and can function as helper viruses without modification. One skilled in the art will also recognize that the helper virus can also be a non-enveloped virus that can infect neurons via axon terminals (such as adenovirus or AAV).

The RG-pseudotyped lentivirus was produced as described (Mazarakis et al., *Hum. Mol. Genet.* 2001; 10(19):2109-2121). Briefly, 293T cells (ATCC, Manassas, Va.) were transfected with LIPOFECTAMINE™ 2000 (Invitrogen, Carlsbad, Calif.) according to the manufacturer's protocol using the following DNA quantities in a 10 cm plate: transfer vector, 2.5 μg; lentiviral packaging construct, 2.5 μg; and rabies virus glycoprotein expression vector, 3 μg. Supernatants were collected 48 and 72 hours post-transfection, pooled, filter sterilized and pelleted by ultracentrifugation for 1 hour at 111,000×g. Pellets were resuspended in 1 ml medium and applied after titering to BHK-21 cells (ATCC) at an MOI of approximately 4 overnight. After four passages, cells were sorted for high GFP fluorescence with a FACSDIVA™ (BD Biosciences, San Jose, Calif.).

Figure 8A:
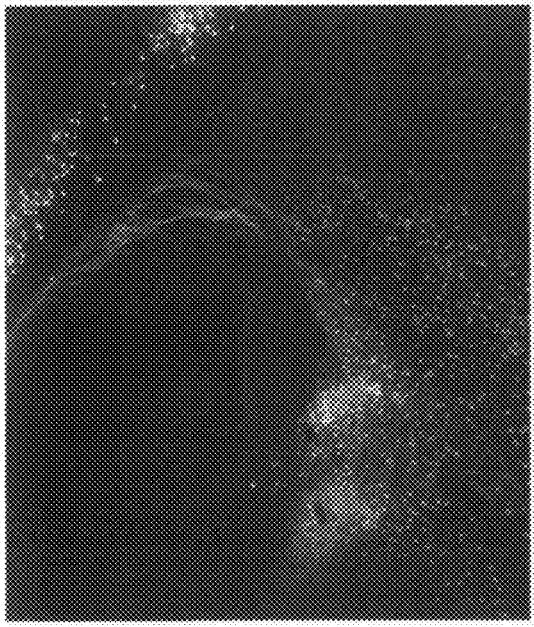
FIG. 8A is a low-power view showing the injection sites in the thalamus (bottom right) as well retrogradely-infected cortical neurons (upper-left).

In one example, the helper virus was an RG-pseudotyped lentivirus which expresses both RG and a nuclear-localized (histone-tagged) GFP. However, one skilled in the art will appreciate that other markers besides GFP can be used. In another example, the AG-rabies had mCherry inserted into its genome rather than GFP (AG-mCherry rabies). The results of using these viruses are illustrated in FIGS. 8A and B. The helper virus (encoding RG and nGFP) was first injected into the visual thalamus of a rat as follows. Animals were anesthetized either with a mixture of ketamine and xylazine or acepromazine and/or with inhaled isoflurane in oxygen. Some animals were intubated while anesthetized in order to deliver isoflurane for maintained anesthesia. A midline scalp incision was made and craniotomies drilled through the skull to expose the brain region of interest. A small cut was made in the dura and a glass pipette or Hamilton syringe filled with virus lowered into the brain. Virus was injected into the brain by pressure. The pipette was removed and the scalp sutured shut. Anesthesia was discontinued and the animal monitored closely until fully recovered. After waiting seven days to allow expression of RG and nGFP in cortical neurons projecting to the thalamus, a AG-mCherry rabies injection was targeted to the same thalamic location using the same methods.

Figure 8B:
FIG. 8B is a higher-power view of retrogradely infected cortical neurons. Rabies-infected cells are completely filled with mCherry, while nGFP expressed from retrograde infection with the RG-pseudotyped lentivirus is confined to the nucleus.

FIG. 8A shows injection sites in the thalamus (near the bottom) with both nGFP expression and mCherry expression, as well as many bright red, deep-layer cortical neurons (upper left). A higher power view of the cortex (FIG. 8B) shows that there was successful retrograde expression of both nGFP (from the helper virus) and mCherry (from the AG rabies). However, it is also clear that the two virus injections were not placed at the same site within the thalamus. As a result, there were no cortical neurons that were co-infected and therefore no complementation. mCherry-expressing rabies-infected neurons were restricted to the cortical layers and cell types known to project to the thalamus. This would not be a problem, for example, if both viruses were mixed together and then injected through the same pipette at the same time.

This example illustrates that RG-pseudotyped lentivirus results in efficient retrograde infection, and that the rabies genome can be modified to express mCherry. The slow expression of the lentivirus can be overcome by using other viral vectors that express far more quickly (within 1-2 days). For example, both HSV amplicon vectors and adenovirus can be used as a helper virus instead of lentivirus.

For retrograde infection (see Example 1, for instance), the only gene that needs to be expressed is the rabies virus glycoprotein gene G (or another complementing gene if G-deleted rabies virus is not the TST-defective virus used). Thus, simply expressing the complementing gene in a retrogradely-infectious virus (for instance, adenovirus, HSV, AAV, RV-pseudotyped lentivirus, or even TST-defective rabies virus itself if a different TST-defective virus is being used as the tracing virus) is effective. The complementing gene can be expressed from a promoter that results in expression in neurons, such as the synapsin-1 promoter or a ubiquitously-expressing promoter such as CMV, CAG, or actin. However, in some embodiments, it is useful to co-express a marker gene to easily identify cells infected with the virus, for instance, DsRed2, mCherry, EGFP, or nGFP, a fusion protein of EGFP with a histone so it is nuclearly-localized.

In some examples, a helper virus is used to express one or more genes. For example, to express both genes from the same helper virus, two different cassettes can be used with two different promoters, each driving a separate gene. An IRES (internal ribosomal entry site) also can be used between the two genes to drive both from the same promoter. Alternatively, a different approach can be employed in some embodiments that uses a "2A" sequence between the two genes (Szymczak et al., (2004) *Nat. Biotechnol.* 22(5):589-94); the two genes are then expressed by the same promoter in equimolar ratios. The 2A sequences are short stretches of DNA that encode short peptides that break apart (or fail to bond) during their translation between the second-to-last and last (C terminal) amino acid. Their use involves including one of the 2A sequences between the two genes so that both are frame, and leaving off the stop codon of the upstream, or 5', gene. The promoter produces one long mRNA encoding both genes, and the ribosome translates the very long protein, the first part of which breaks off when the 2A peptide is translated, making two separate proteins as desired.

This approach leaves the cleaved 2A peptide fused to the inner ends of the two proteins: the C terminus of the first protein and the N terminus of the second. The strategy therefore depends on the ability of the two proteins to tolerate these small modifications. The upstream protein is modified more than the downstream one, since the peptide cleaves right before the last amino acid: the downstream protein (3' gene) therefore only has one extra amino acid added to its N terminus, while the upstream one (5' gene) has more extensive modifications: a dozen or more amino acids added to its C terminus. Thus, the gene order can make a difference depending on the particular gene used.

Since modifications to the rabies virus glycoprotein's C terminus are not well tolerated, the 2A constructs included this gene last (3') (if it was included at all; for controls it was left out), so that the glycoprotein's C terminus is not modified at all, and its N terminus only has one extra amino acid. Therefore, in some examples the rabies virus glycoprotein G was in the 3' position in the helper virus construct (for example EGFP-2A-G). Also, since the TVA gene (when included) is somewhere other than in the 3' position, it will therefore suffer a modification to its C terminus. Thus, the transmembrane isoform ("TVA950") was used, as opposed to its GPI-anchored one ("TVA800") (see, for instance, Narayan et al., (2003) *J. Virol.* 77(3):1977-83). Without being bound by theory, it is believed that TVA950 is more tolerant of C-terminal modifications that TVA800.

Any one of a number of 2A sequences can be used (Szymczak et al., (2004) *Nat. Biotechnol.* 22(5):589-94). In one embodiment, the "F2A" sequence was used for the bicistronic (two gene) cassettes, and the "F2A" and "T2A" sequences were used for the tricistronic ones.

For the retrograde helper strategy, one exemplary expression cassette is a synapsin, CMV, CAG, or actin promoter driving mCherry-2A-G, DsRed2-2A-G, nGFP-2A-G, or EGFP-2A-G. Lentiviruses were generated with the first three of these.

For the cre-dependent helper strategy, one exemplary expression cassette is: a promoter (as above) followed by a loxP site, followed by the 2A-linked set of genes in the opposite orientation with respect to the promoter, followed by a second lox site that is in opposite orientation with respect to the first lox site. Cre acting on these oppositely-oriented lox sites will invert the stretch of DNA that is between them (and keep on inverting ad infinitum, but 50% of the time the gene will be in the forward orientation and able to be transcribed).

If TVA is included (for example in a retrogradely infecting helper virus, such as one that includes a cre or other appropriate recombinase site), projection neurons can be targeted by injecting the helper virus in their projection target nuclei, then injecting EnvA-pseudotyped virus back in the vicinity of their cell bodies once they express TVA. Exemplary expression cassettes that were generated include TVA950-2A-G, DsRed2-2A-TVA950-2A-G, mCherry-2A-TVA950-2A-G, and nGFP-2A-TVA950-2A-G. However, one skilled in the art will recognize that the positions of TVA and the fluorophore can be interchanged, for instance, TVA950-2A-nGFP-2A-G. For controls, the glycoprotein can be omitted, for instance, nGFP-2A-TVA. When two 2A sequences are used in one cassette, for instance, to separate three genes, two different 2A sequences (F2A and T2A) were used.

All of the helper viruses described herein were made using published techniques (for instance, see Tiscornia et al. (2006) *Nat. Protoc.* 1(1):241-5, for lentivirus).

In some embodiments, HSV amplicon vectors or adenovirus are injected into barrel cortex using the same injection method described above, and then labeling is assayed in the opposite hemisphere. Callosally-projecting neurons are directly infected, and the rabies spreads one synapse further following trans-complementation.

In other embodiments, multiple genes (e.g., 2 or more genes, or 3 or more genes) in a helper virus are expressed under the control of a single promoter. For instance, in some examples, "IRES-like" elements, which are self-cleaving 2A sequences from foot-in-mouth disease virus, are used (Chinnasamy et al., *Virol J* 2006; 3:14). The mRNA which codes for all concatenated genes, separated by 2A sequence, is transcribed continuously, assuring near-equimolar production for all genes. The peptide sequences are cut during translation. There are small modifications of the 5' peptide chains for all but the last gene in the sequence. This method was used to express both nGFP and RG in the lentiviral helper described above, and it is the method used in the descriptions below for expression of three genes from cre-dependent lentivirus (Example 5B). Small modifications in the peptide sequence do not affect the function of any of the proteins used herein.

B. Helper Viruses that Express TVA and RG Following cre Recombination

This method permits tracing of neurons that provide direct synaptic input to a specific cell type that expresses cre-recombinase (or other recombinase, such as Flp, Tn3, or PhiC31, or the recombinase of a DNA transposon). Cre-recombinase has become a prevalent tool to obtain selective gene expression in specific cell types. For example, numerous mouse lines are available for use in developmental studies. In addition, cre-recombinase can be expressed from viral vectors or in electroporated cells so that it can be utilized in non-transgenic animals. In one embodiment, helper viruses are used that express EnvA (see Example 2), RG, and a marker protein (for instance, nGFP) only in cells which express a desired recombinase (e.g., cre or Flp).

One such helper virus is a cre-dependent lentivector. The design of this and other cre-dependent helper viruses has carefully considered unique aspects of the viral life cycles for each type of vector. These factors have the potential to influence how the vector behaves when STOP sequences and loxp sites are present. For example, a typical cre-dependent construct incorporates a promoter, followed by a floxed STOP sequence, and then the gene(s) to be expressed. Following infection, the lentivirus delivers RNA, which is reverse transcribed and integrated in the host cell, raising the possibility that the STOP sequence will interfere with the incorporation of full-length copies. To overcome this potential problem, a novel strategy was employed in which the coding sequence for the gene(s) was introduced in reverse orientation (reverse ORF, designated as FRO). Flanking loxp sites were introduced in an orientation which results in cre-dependent excision and reinsertion in a random orientation. Thus, half of the copies are reinserted in the ORF rather than the FRO orientation. Because each neuron is infected with multiple viral copies, expression from just half the copies is sufficient. This method results in far tighter regulation than with typical floxed STOP sequences, which can be "leaky". Thus, even if this strategy is not necessary (conventional floxed STOP sequences do appear to work with lentivirus) it is an improvement.

Figures 9A, 9B:
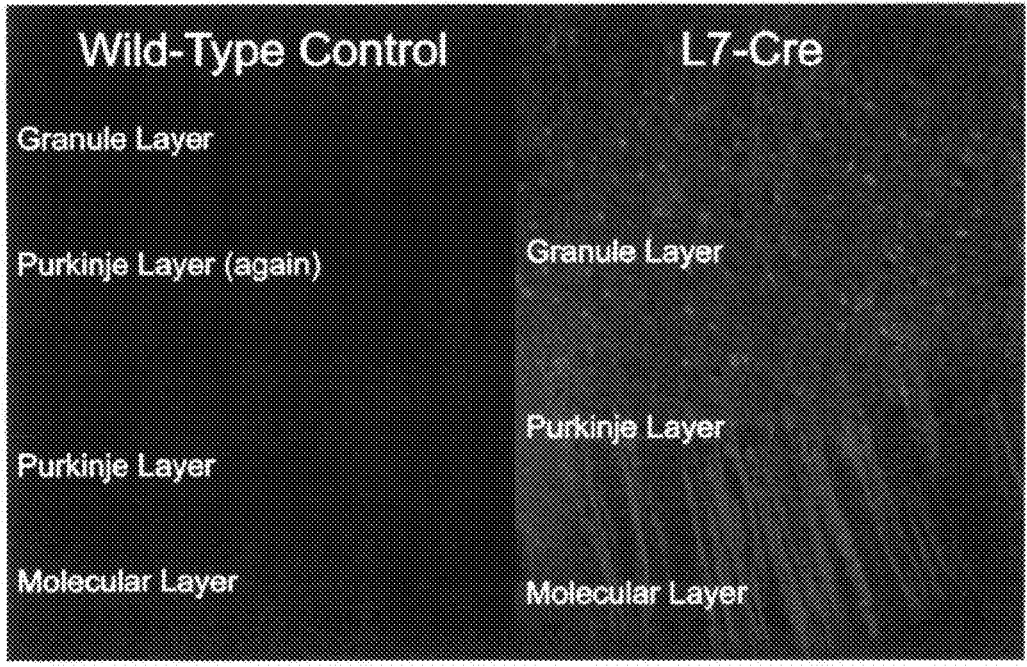
FIG. 9A illustrates the results observed following injections in a wild-type mouse. In the wild-type control no GFP expression was observed. This indicates that there was no expression of TVA (as expected due to the intended requirement for cre-recombination to allow TVA expression) and there was no spurious rabies infection of non-TVA expressing neurons.
FIG. 9B shows comparable injections in L7-Cre mice. Numerous GFP-expressing cerebellar Purkinje cells and granule cells are visible. The cell bodies of Purkinje cells are visible, as well as their apical dendrites extending into the molecular layer. The somata of granule cells are also visible in the granule layer, as well as their axons coursing through the molecular layer perpendicular to the plane of the Purkinje cell dendrites. These are the results expected from the selective expression of TVA in cre-expressing Purkinje cells following helper virus injection. Subsequent injection of EnvA-dG-GFP rabies presumably resulted in selective infection of Purkinje cells. Transcomplemention due to RG expression in the same Purkinje cells allowed transsynaptic spread of the rabies virus to the granule cells, which are known to be directly presynaptic to Purkinje cells. Additional GFP expression was also observed in other cell types known to be presynaptic to Purkinje cells.

Cre-dependent, helper lentivirus were used to label inputs to specific cell types in two different cre-expressing mouse lines, L7-Cre and DAT-Cre (Dopamine Transporter). The mouse cerebellum was injected with the cre-dependent helper lentivirus expressing TVA and RG. Seven days later, EnvA-ΔG-GFP rabies was injected at the same site. Five days after that the animals were perfused and cerebellar sections examined for GFP expression. Typical results for L7-Cre mice are illustrated in FIG. 9B (with control shown in FIG. 9A). In these mice, cre-recombinase is expressed selectively in cerebellar Purkinje cells. The helper virus incorporated the CMV promoter followed by floxed reverse ORF sequences for myc-tagged TVA, 2A sequence, RG. The myc tag was intended to allow independent visualization of TVA expression, but antibodies did not reveal TVA, despite clear evidence of TVA expression. (For instance, EnvA-ΔG-GFP Rabies infection only occurred following injection of helper virus, and did not occur when no TVA-expressing lentivirus had been injected; see FIG. 9).

Additional cre-dependent helper viruses that can be used with this method include, but are not limited to, AAV, HSV amplicon, adeno-associated, and adenoviral vectors. The HSV amplicons and adenoviral vectors are particularly useful, since they result in relatively fast expression, and thus can be used, for example, in developmental studies. However, the AAV and lentiviral vectors also incorporate good temporal control when combined with the use of transgenic mice or other vectors expressing inducible cre-recombinase (for instance, Cre-ER2; Matsuda & Cepko, *Proc Natl Acad Sci USA* 2007; 104(3):1027-1032). In this case, gene expression and subsequent trans-complementation is quickly induced with tamoxifen.

Example 6

Incorporation of Other Genes into the Rabies Genome

This Example describes methods that can be used to incorporate heterologous genes into the genome of a TST-defective virus (such as the G-deleted rabies virus described herein). These genes are then expressed in neurons that are presynaptic to specific cell types. Exemplary genes include, but are not limited to, marker genes (for instance, GFP, EGFP, mCherry, LacZ, Dendra-2), genes to allow manipulation of activity (for instance, ChR2, NpHR, Kir2.1), genes to monitor activity (for instance, genetically expressed $Ca^{++}$ sensors), and genes to allow temporal control of viral spread (for instance, Cre-ER2, inducible cre recombinase).

The utility of the monosynaptically restricted tracing methods described herein can in some examples be enhanced by incorporating novel into the genome of the TST-defective virus. This not only allows the marking of synaptically connected networks, but also the manipulation and/or monitoring of the activity of these neurons.

As described herein, the following genes were cloned into the rabies genome: EGFP, mCherry, Cre-ER2, ChR2, TN-XL (troponin-based calcium sensor). Other genes that can be incorporated into a rabies genome, include, but are not limited to: LacZ, Dendra-2, Kir2.1, nGFP, NpHR, and chameleon-FP (a calcium sensor). However, one skilled in the art will recognize that any gene of interest can be cloned into the rabies genome.

It is not straightforward to modify the rabies genome because rabies is a negative strand RNA virus that does not use DNA at any stage in its life cycle. However, nearly all of the available methods for manipulating genetic material use DNA. Thus, it was necessary to generate and then manipulate a series of DNA plasmids and then successfully "rescue" viable rabies particle. (See, for instance, Finke & Conzelman (1999) *J. Virol.* 73(5):3818-25). Using this method, the following have been inserted into the rabies virus genome: EGFP, mCherry, Cre-ER2, ChR2, and TN-XL.

For two genes tested (including ChR2), the viral titers were low, and when neurons were infected in vivo, the numbers of transduced cells were low. Without being bound by theory, it is believed that this was due to the very high levels of gene expression achieved with replication competent rabies virus, and that genes that can induce moderate toxicity reduce the health of the cell lines used for viral production. This problem can be solved using exemplary strategies. One is to alter the placement of the coding sequences within the viral genome. Because regulation of transcription is dependent on position, moving the gene to a position with lower transcription levels improves viral titers. A second strategy involves placing an IRES sequence upstream of the gene. Since conventional IRES elements are translated inefficiently, this reduces protein levels.

Example 7

Multisynaptic and Temporally Regulated Tracing

This Example describes methods that can be used to label circuits across multisynaptic pathways and for monitoring changes in connectivity over time, and describes one of many possible scenarios for how these can be used for temporally-regulated tracing of neuronal connections across mutisynaptic pathways. In one example, a ΔG-rabies virus expressing both Cre-ER2 and a photoconvertible fluorescent protein (Dendra-2; Gurskaya et al., *Nat. Biotechnol.* 2006; 24(4): 461-465) was used. This allowed temporal control of viral spread, and allowed the state of the circuit to be marked with different colors at different developmental timepoints and/or at different stages of multisynaptic transsynaptic spread.

In one embodiment, to allow controlled multisynaptic spread of rabies virus and differential labeling at defined synaptic steps, rabies viral expression of tamoxifen-inducible cre-recombinase (Cre-ER2 [12]) and Dendra-2 is used. This is combined with use of transgenic animals conditionally expressing RG following cre-recombination. For example, in one embodiment, in a starting cell population (cell group 1) TVA (but not RG) is expressed using a helper virus (for instance, see Example 5). Following expression of the TVA, these cells are selectively infected with EnvA-dG-Cre-ER2/Dendra-2 rabies. This results in rabies infection and expression of both Cre-ER2 and Dendra-2 selectively in cell group 1. However, due to the lack of RG in any cells, there is no transcomplementation or spread of the rabies virus. At the desired timepoint, however, administration of tamoxifen allows transient nuclear localization of the Cre-ER2 and recombination, resulting in RG expression selectively in cell group 1. Transcomplementation then results in transsynaptic spread of the rabies virus to presynaptic neurons (cell group 2). This results in expression of the rabies genes, including Cre-ER2 and Dendra-2 in both cell groups. Thus, cell group 1 uniquely expresses TVA and Dendra-2, while cell group 2 expresses only Dendra-2. At this time, the Dendra-2 is in its green fluorescent state. However, exposure to blue light converts the Dendra-2 to red. Thus cell groups 1 and 2 are labeled red and continue to accumulate green Dendra-2. Administration of tamoxifen at the same time results in RG expression and transcomplementation in cell group 2, and spread of rabies to neurons directly presynaptic to these cells (cell group 3). The cells in group 3 express only the green form of Dendra-2. Subsequent sacrifice and perfusion of the animals followed by antibody staining for TVA (blue secondary antibody) results in unique identification of all 3 cell groups. Only group 1 is labeled blue (anti-TVA), and it also has red and green Dendra-2. Cell group 2 contains red and green Dendra-2, but no blue TVA. Cell group 3 contains only green Dendra-2.

This particular example describes one of many possible strategies for the use of these reagents. It should be apparent, however, that there are many other possible ways to use these as well as the other reagents described in the previous Examples to achieve the many and varied results, particularly in studying the development of synaptic connectivity.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A method for monosynaptic transport of a heterologous nucleic acid sequence, comprising:
   contacting one or more primary neurons, each of which is connected by a plurality of synapses to a plurality of secondary neurons, with:
   (i) a transsynaptic transport (TST)-defective virus (TST-defective virus), wherein the TST-defective virus is defective for transport across the plurality of synapses and comprises a heterologous nucleic acid sequence; and
   (ii) one or more nucleic acid molecules encoding one or more polypeptides that complement in trans the TST-defective phenotype of the TST-defective virus,
   wherein the secondary neurons do not contain the nucleic acid molecules encoding one or more polypeptides that complement in trans the TST-defective phenotype of the TST-defective virus,
   under conditions that permit expression of the polypeptide(s) in the primary neuron(s), rescue of the TST-defective phenotype by the polypeptide(s) in the primary neuron(s), and
   thereby monosynaptically transporting the TST-defective virus comprising the heterologous nucleic acid sequence from the primary neuron(s) to the plurality of secondary neurons across the plurality of synapses.

2. The method of claim 1, wherein the one or more primary neurons are post-synaptic to the plurality of secondary neurons.

3. The method of claim 1, wherein the TST-defective virus is transported retrogradely from the primary neuron(s) to the plurality of secondary neurons.

4. The method of claim 1, wherein the TST-defective virus is transported anterogradely from the primary neuron(s) to the plurality of secondary neurons.

5. The method of claim 1, wherein the TST-defective virus is an RNA virus.

6. The method of claim 5, wherein the RNA virus is a negative-strand ssRNA virus.

7. The method of claim 5, wherein the RNA virus is a member of the Family Rhabdoviridae.

8. The method of claim 5, wherein the RNA virus is of the genus Lyssavirus.

9. The method of claim 5, wherein the RNA virus is a rabies virus.

10. The method of claim 1, wherein the TST-defective virus lacks at least one envelope protein.

11. The method of claim 10, wherein the at least one envelope protein is a glycoprotein.

12. The method of claim 10, wherein the polypeptide is a glycoprotein of the virus.

13. The method of claim 1, wherein the heterologous nucleic acid sequence encodes a detectable polypeptide, a polypeptide that affects a function of primary neurons or secondary neurons, a polypeptide useful for monitoring a function of primary neurons or secondary neurons, or an inhibitory RNA (RNAi).

14. The method of claim 1, further comprising detecting the TST-defective virus.

15. The method of claim 14, wherein detecting comprises contacting the primary neuron(s) and the plurality of secondary neurons with a binding agent specific for a non-host polypeptide encoded by the TST-defective virus or specific for a non-host nucleic acid sequence of the TST-defective virus.

16. The method of claim 15, wherein the binding agent is an antibody specific for the non-host polypeptide.

17. The method of claim 16, wherein the non-host polypeptide is an envelope protein.

18. The method of claim 17, wherein the envelope protein is a glycoprotein.

19. The method of claim 18, wherein the TST-defective virus is detected substantially only in the primary neuron(s) and the plurality of secondary neurons.

20. The method of claim 1, wherein the one or more polypeptides are not substantially expressed in neurons in the absence of the one or more nucleic acid molecules.

21. The method of claim 1, wherein the one or more polypeptides are viral polypeptides that are not substantially expressed in neurons in the absence of the one or more nucleic acid molecules.

22. The method of claim 1, wherein the one or more primary neurons is a single neuron.

23. The method of claim 1, wherein the TST-defective virus is microinjected into the primary neuron(s).

24. The method of claim 1, wherein the TST-defective virus further comprises a foreign envelope protein.

25. The method of claim 24, wherein the foreign envelope protein is a glycoprotein of a non-neurotropic virus.

26. The method of claim 24, wherein the foreign envelope protein is a chimeric glycoprotein comprising the cytoplasmic domain of the rabies virus glycoprotein and the extracellular and transmembrane domains of a glycoprotein of a non-neurotropic virus.

27. The method of claim 25, wherein the non-neurotropic virus is avian sarcoma and leucosis virus subgroup A (ASLV-A).

28. The method of claim 24, wherein the one or more primary neurons are further contacted with a nucleic acid molecule encoding a receptor specific for the foreign envelope protein.

29. The method of claim 25, wherein contacting the one or more primary neurons with the one or more nucleic acid molecules comprises contacting the one or more primary neurons with a helper virus comprising the one or more nucleic acid molecules, wherein the helper virus is incapable of TST or is TST-defective and is not trans complemented in the primary neuron.

30. The method of claim 29, wherein the helper virus is an adenovirus, an HSV amplicon vector, or a lentivirus incapable of TST or TST-defective and is not trans complemented in the primary neuron.

31. The method of claim 30, wherein the helper virus is a cre-dependent virus or an HSV amplicon vector incapable of TST or TST-defective and is not trans complemented in the primary neuron.

32. The method of claim 31, wherein the helper virus is a cre-dependent lentivirus or a cre-dependent adenovirus incapable of TST or TST-defective and is not trans complemented in the primary neuron.

* * * * *

UNITED STATES PATENT AND TRADEMARK OFFICE
CERTIFICATE OF CORRECTION

PATENT NO. : 7,785,874 B2
APPLICATION NO. : 12/008604
DATED : August 31, 2010
INVENTOR(S) : Wickersham et al.

It is certified that error appears in the above-identified patent and that said Letters Patent is hereby corrected as shown below:

In the Specification:

Column 24, line 20, "AgGACcC" should read --AgGAccC--

Column 24, line 45, "GTTCCTCAGGTCCT" should read --GTTCCTCAGGTCCT--

Column 24, line 48, "TAA" should read --TAA--

Column 25, line 5, "ATG" should read --ATG--

Column 25, line 9, "TAA" should read --TAA--

Column 31, line 49, "AG-GFP" should read --ΔG-GFP--

Column 32, line 7, "AG-GFP" should read --ΔG-GFP--

Column 32, lines 10 and 43, "AG-rabies" should read --ΔG-rabies--

Column 32, line 44, "(AG-mCherry rabies)" should read --ΔG-mCherry rabies)--

Column 32, line 60, "AG-mCherry rabies" should read --ΔG-mCherry rabies--

Column 33, line 1, "AG" should read --ΔG--

Column 35, line 51, "AG-GFP" should read --ΔG-GFP--

Column 35, line 61, "EnvA-AG-GFP" should read --EnvA-ΔG-GFP--

Signed and Sealed this
Tenth Day of May, 2011

David J. Kappos
*Director of the United States Patent and Trademark Office*

SEQUENCE LISTING

```
<160> NUMBER OF SEQ ID NOS: 11

<210> SEQ ID NO 1
<211> LENGTH: 33
<212> TYPE: DNA
<213> ORGANISM: Artificial
<220> FEATURE:
<223> OTHER INFORMATION: forward primer

<400> SEQUENCE: 1
tttcagcggc cgcatggaag ccgtcataaa ggc                               33

<210> SEQ ID NO 2
<211> LENGTH: 46
<212> TYPE: DNA
<213> ORGANISM: Artificial
<220> FEATURE:
<223> OTHER INFORMATION: reverse primer

<400> SEQUENCE: 2
aggttctgat cgattgactc ttctgcaagg caggcacact actagc                 46

<210> SEQ ID NO 3
<211> LENGTH: 46
<212> TYPE: DNA
<213> ORGANISM: Artificial
<220> FEATURE:
<223> OTHER INFORMATION: forward primer
```

<400> SEQUENCE: 3
gctagtagtg tgcctgcctt gcagaagagt caatcgatca gaacct        46

<210> SEQ ID NO 4
<211> LENGTH: 35
<212> TYPE: DNA
<213> ORGANISM: Artificial
<220> FEATURE:
<223> OTHER INFORMATION: reverse primer

<400> SEQUENCE: 4
gacggcggat cctcacagtc tggtctcacc cccac        35

<210> SEQ ID NO 5
<211> LENGTH: 43
<212> TYPE: DNA
<213> ORGANISM: Artificial
<220> FEATURE:
<223> OTHER INFORMATION: primer

<400> SEQUENCE: 5
actattaaca tccctcaaag gacccaagga aagatggttc ctc        43

<210> SEQ ID NO 6
<211> LENGTH: 41
<212> TYPE: DNA
<213> ORGANISM: Artificial
<220> FEATURE:
<223> OTHER INFORMATION: primer

<400> SEQUENCE: 6
ttttctcgac tgaaaagcta gcatgaccca gcactttata a        41

<210> SEQ ID NO 7
<211> LENGTH: 46
<212> TYPE: DNA
<213> ORGANISM: Artificial
<220> FEATURE:
<223> OTHER INFORMATION: primer

<400> SEQUENCE: 7
ttaacatccc tcaaaagact caaggaaaga tggttcctca ggtcct        46

<210> SEQ ID NO 8
<211> LENGTH: 477
<212> TYPE: DNA
<213> ORGANISM: Artificial
<220> FEATURE:
<223> OTHER INFORMATION: nucleotide sequence around the transcription
      stop and polyadenylation signal of the G gene in pSAD L16

<400> SEQUENCE: 8
agactgtaag gactggccgt cctttcaacg atccaagtcc tgaagatcac ctcccttgg    60 ggggttcttt ttgaaaaacc tgggttcaat agtcctcctt gaactccatg caactgggta   120
gattcaagag tcatgagatt ttcattaatc ctctcagttg atcaagcaag atcatgtcga   180
ttctcataat aggggagatc ttctagcagt ttcagtgact aacggtactt tcattctcca   240
ggaactgaca ccaacagttg tagacaaacc acggggtgtc tcgggtgact ctgtgcttgg   300
gcacagacaa aggtcatggt gtgttccatg atagcggact caggatgagt taattgagag   360
aggcagtctt cctcccgtga aggacataag cagtagctca caatcatctc gcgtctcagc   420
aaagtgtgca taattataaa gtgctgggtc atctaagctt ttcagtcgag aaaaaaa      477

-continued

```
<210> SEQ ID NO 9
<211> LENGTH: 46
<212> TYPE: DNA
<213> ORGANISM: Artificial
<220> FEATURE:
<223> OTHER INFORMATION: nucleotide sequence around the PpuMI
      recognition site in pSADdeltaG

<400> SEQUENCE: 9
ttaacatccc tcaaaggacc cgctagcttt tcagtcgaga aaaaaa                    46

<210> SEQ ID NO 10
<211> LENGTH: 46
<212> TYPE: DNA
<213> ORGANISM: Artificial
<220> FEATURE:
<223> OTHER INFORMATION: nucleotide sequence around the transcriptional
      start and translation initiation sites of the EGFP gene in
      pSADdeltaG-EGFP

<400> SEQUENCE: 10
ttaacatccc tcaaaggacg ggatccatcg ccaccatggt gagcaa                    46

<210> SEQ ID NO 11
<211> LENGTH: 46
<212> TYPE: DNA
<213> ORGANISM: Artificial
<220> FEATURE:
<223> OTHER INFORMATION: nucleotide sequence around the transcription
      stop and polyadenylation signal of the EGFP gene in
      pSADdeltaG-EGFP

<400> SEQUENCE: 11
tacaagtaaa gcggccgacc cgctagcttt tcagtcgaga aaaaaa                    46
```